United States Patent [19]
Jacobsen et al.

[11] Patent Number: 6,033,784
[45] Date of Patent: Mar. 7, 2000

[54] METHOD OF PHOTOCHEMICAL IMMOBILIZATION OF LIGANDS USING QUINONES

[76] Inventors: Mogens Havsteen Jacobsen, Alekistevej 225, 1, DK-2770, Vanløse; Troels Koch, Funkiavej 47, DK-2300, Copenhagen S, both of Denmark

[21] Appl. No.: 08/930,623

[22] PCT Filed: Apr. 3, 1996

[86] PCT No.: PCT/DK96/00167

§ 371 Date: Oct. 7, 1997

§ 102(e) Date: Oct. 7, 1997

[87] PCT Pub. No.: WO96/31557

PCT Pub. Date: Oct. 10, 1996

[51] Int. Cl.[7] .................... B05D 3/06; B05D 1/36
[52] U.S. Cl. .................. 428/411.1; 427/2.1; 427/2.11; 427/2.13; 427/520; 427/558; 427/508; 427/581; 428/414; 428/415; 428/426; 435/4; 435/7.1; 435/283.1; 435/285.1; 435/174; 435/304.1; 435/305.1
[58] Field of Search .................. 427/2.1, 2.11, 427/2.13, 520, 558, 581, 508; 428/411.1, 414, 415, 426; 424/407, 409, 423, 9.1; 435/4, 7.1, 305.1, 304.1, 283.1, 285.1, 174

[56] References Cited

U.S. PATENT DOCUMENTS

Re. 31,712  10/1984  Geise ........................... 427/2.1
Re. 32,991  7/1989  Szycher et al. ................ 427/2.31

(List continued on next page.)

FOREIGN PATENT DOCUMENTS

| | | |
|---|---|---|
| 0 319 953A2 | 6/1989 | European Pat. Off. |
| 0 319 957A2 | 6/1989 | European Pat. Off. |
| 0 155 252A2 | 9/1995 | European Pat. Off. |
| 63-271410A | of 1988 | Japan |
| WO 89/05616 | 6/1989 | WIPO |
| WO 91/02768 | 3/1991 | WIPO |

OTHER PUBLICATIONS

Carey, Francis A. et al., "Part A: Structure and Mechanisms," *Advanced Organic Chemistry*, A Plenum Press, NY, pp. 467–468 (1977).

Furniss, Brian S. et al., "Vogel's Textbook of Practical Organic Chemistry," Fifth Edition, Longman Scientific & Technical, UK, p. 109 (1989).

Jakobsen, Mogens Havsteen, "Photochemical Grafting of Functional Groups and Biomolecules Onto Polymer Surfaces," Center for Medical Biotechnology, University of Copenhagen (Apr. 27, 1995).

Analytical and Technical Application of Functional Materials, Abstracts (1995).

Jakobsen, Mogens Havsteen et al., "Immobilization of Histidine Tagged Peptides on Nickel Chelate Derivatized Microtitre Plates," 4th International Symposium, UK, pp. 1–7 (1995).

Jensen, Soren Peter et al., "Photochemical Coupling of Peptides to Polystyrene Microwell Plates," *Innovation and Perspectives in Solid Phase Synthesis & Combinatorial Libraries*, pp. 419–422 (1996).

"Enzyme Immunoassay: Binding of Salmonella Antigens to Activated Microtiter Plates", Aleixo et al., Journ. of Immunoassay 6(4), (1985), pp. 391–407. (No Month).

*Primary Examiner*—Diana Dudash
*Attorney, Agent, or Firm*—Finnegan, Henderson, Farabow, Garrett & Dunner, L.L.P.

[57] ABSTRACT

A method of immobilizing a ligand (L) to the surface (P) of a carbon-containing substrate material; said method comprising: a photochemical step of linking of one or more photochemically reactive compounds (Q) to a carbon-containing material surface (P); wherein the photochemically reactive compound (Q) is a quinone compound containing a cyclic hydrocarbon, or from 2 to 10 fused cyclic hydrocarbons, with at least two conjugated carbonyl groups; and wherein the photochemical step comprises irradiation of the photochemically reactive compound (Q) with non-ionizing electromagnetic radiation having a wavelength in the range from UV to visible light.

34 Claims, 30 Drawing Sheets

U.S. PATENT DOCUMENTS

| | | | |
|---|---|---|---|
| 3,891,327 | 6/1975 | Welch | 427/4 |
| 4,016,306 | 4/1977 | Miyagawa et al. | 427/508 |
| 4,722,906 | 2/1988 | Guire | 436/501 |
| 4,737,544 | 4/1988 | McCain et al. | 427/2.1 |
| 4,822,682 | 4/1989 | Dorsch et al. | 427/162 |
| 4,892,402 | 1/1990 | Sawamoto et al. | 351/160 H |
| 4,973,493 | 11/1990 | Guire | 427/2 |
| 5,002,582 | 3/1991 | Guire et al. | 623/66 |
| 5,292,873 | 3/1994 | Rokita et al. | 536/24.3 |
| 5,304,404 | 4/1994 | Morra et al. | 427/512 |
| 5,378,502 | 1/1995 | Willard et al. | 427/305 |
| 5,391,438 | 2/1995 | Pasternak | 427/322 |
| 5,409,731 | 4/1995 | Nakagawa et al. | 427/2.12 |
| 5,427,779 | 6/1995 | Elsner et al. | 427/2.1 |
| 5,466,492 | 11/1995 | Kiessling et al. | 427/117 |
| 5,482,867 | 1/1996 | Barrett et al. | 427/2.13 |
| 5,545,568 | 8/1996 | Ellman | 427/2.1 |

(I)
 (II)
 (III)
 (IV)
 (V)
 (VI)
 (VII)
 (VIII)
 (IX)
 (X)

(XI)

(XII)

(XIII)

(XIV)

(XV)

(XVI)

(XVII)

(XVIII)

(XIX)

(XX)

(XXI)

(XXII)

(XXIII)

(XXIV)

(XXV)

(XXXVII)

(XXXVIII)

(XXXIX)

(1)

(2)

(3)

(4)

(5)

(6)

(7)

(8)

(9)

(10)

(11)

(12)

(13)

(14)

(19)

(20)

(21)

n ≈ 43

(22)

METHOD OF PHOTOCHEMICAL IMMOBILIZATION OF LIGANDS USING QUINONES

BACKGROUND OF THE INVENTION

The present invention relates to a method of modifying a polymer surface by covalent attachment of functional compounds, also designated ligands.

1. The Technical Field

Products made of synthetic or natural polymers having modified surfaces are very important in many technical areas.

Surface modification of polymers by the introduction of various functional groups or the covalent attachment of biologically active molecules has been the subject of increased research in recent years in such different areas as the development of novel biocompatible implants, for biosensors and biomaterials, for affinity chromatography, for surface resistant materials, for biosensors, and for covalent immobilization of high or low molecular weight molecules in ELISA assays.

2. Prior Art

Thermochemical Methods

Most methods involve sequential treatment of the polymer surface with chemical reagents to introduce functional groups to function as handles for coupling of a functional compound also called ligand. However, these methods usually employ hazardous chemicals and several time-consuming steps. In addition to this, only a limited number of methods are described in which the mechanical and optical properties of the polymer can be preserved. A method of introducing primary amino groups onto polystyrene tubes using thermochemical reactions and onto microtitre plates has been described by Alexio, J. A. G.; Swaminathan, B; Minnich, S. A.; Wallshein, V. A.; J. Immunoassay 1985, 6, 391–407.

Radioanalytical Methods

EP-A-O 155 252 discloses a method of preparing an immunoreactive solid phase wherein a biologically active molecule is covalently bound to functional groups of vinyl monomers radiation grafted to a solid polymer surface. Grafting requires an adequate radiation dose under an inert atmosphere using radiation such as ultraviolet or ionizing radiation. Specific examples using 0,25 Mrad/h $^{60}$Co irradiation source for 10–12 hours are given.

International application no. WO 91/02768 discloses radio-derivatized polymers produced by contacting non-polymerizable conjugands, such as quinones or compounds from which quinones or quinoid structures are generated during radio-derivatization, with radiolyzable polymers, such as polystyrene, in the presence of high energy gamma rays. The radio-derivatized polymers are suitable for introducing anchoring groups for covalent immobilization or for fixing of molecules on polymer surfaces with or without cross-linkers or with activators such as carbodiimides.

A disadvantage of radio-derivatization is the use of ionizing high energy gamma rays which requires costly health physical precautions in carrying out the method.

Photochemical Methods

A number of photochemical methods of modifying polymer surfaces are also known. In these methods a desired ligand (L)—often a sensitive biomolecule—is immobilized on the polymeric material surface (P) through a photochemically reactive group (Q) and a spacer (S) and optionally a thermochemical reactive group (T).

In general, the covalent attachment of the desired molecule (L) to the surface can be established in three ways:

1) The photochemically reactive group (Q) which is coupled—via a spacer (S)—to a thermochemical reactive group (Q-S-T) is bound covalently to the surface (P) by a photochemical reaction (P-Q-S-T). Subsequently, the desired molecule (L) is coupled to the surface (P-Q-S-T) by thermochemical reaction (P-Q-S-T-L).

2) The photochemically reactive group (Q) which is coupled directly—via a spacer (S)—to the desired molecule (Q-S-L) is bound to the surface (P) by a photochemical reaction (P-Q-S-L).

3) The photochemically reactive group (Q) is coupled covalently to the surface (P) by a thermochemical reaction (P-Q). Subsequently, the desired molecule (L) is coupled to the surface (P-Q) by a photochemical reaction (P-Q-L).

The first two strategies are potentially the most flexible ones and allow control of the orientation of the immobilized ligand.

EP-A2-0 319 953 discloses a photochemical method of modifying a polymer surface by immobilizing an optionally substituted two or three membered heterocyclic compound to the surface of the polymer using electromagnetic irradiation with a wavelength shorter than 700 nm. Preferred compounds are optionally substituted coumarins, benzofurans, indols, and angelicins. Particularly, optimally substituted psoralens are preferred.

A disadvantage of this method is that psoralens are multifunctional compounds which are not easy to synthesize. They are expensive and not chemically stable, e.g. spacers containing primary amines (as a functional group) can not be introduced onto the surface, because the amine will react with the psoralen.

When irradiated with UV light having a short wavelength, a secondary amine placed in the end position and coupled—via a spacer—to psoralen can be photochemically bound to a polystyrene surface. When biotin is coupled to the spacer derivative, biotin can also be photochemically bound to polystyrene surfaces and polymethyl-methacrylate particles. The method cannot be considered to be generally applicable, as only these two examples work satisfactorily. The photochemical mechanism has not been fully understood, but it is known that psoralen derivatives react with double bonds in a 2+2 cyclo addition reaction when irradiated with UV light.

A number of patent publications U.S. Pat. Nos. 4,722,906, 4,973,493, 5,002,582 and PCT/US88/04491, assigned to Biometric Systems Inc., disclose methods for photochemical modification of polymer surfaces. The patent publications essentially describe methods involving activating latent reactive groups selected from the group consisting of those able to generate free radicals, carbenes, nitrenes and exited states of ketones, and covalently bonding thereof to a solid surface.

The disclosed latent reactive groups responsive to ultra-violet, visible or infrared portions of the electromagnetic spectrum are: azides, acylazides, azido formates, sulfonyl azides, phosphoryl azides; diazo compounds such as diazoalkanes, diazoketones, diazoacetates, beta-ketone-alpha-diazoacetates; aliphatic azo compounds, diazirines, ketone, diphenylketone and photoactivable ketones such as benzophenone and acetophenone; and peroxy compounds such as dialkyl- and diacyl peroxides and peroxyesters.

Latent reactive groups, which upon irradiation with high energy UV light generates highly reactive radicals, carbenes or nitrenes, suffer from a number of drawbacks. Such species are extremely reactive and will either rear-range or immediately react with most organic compounds, organic solvents and water. When the irradiation takes place in a solution, this results in loss of photoreagent and ineffecient or reaction with the polymer surface. The simple precursors requires long irradiation times (typically 12 hours) which makes the application of these as photoreactive groups time consuming, inefficient and not suitable for immobilization of sensitive biomolecules.

Nothing is indicated nor suggested about photochemical coupling using quinones as the photoreactive group.

DISCLOSURE OF THE INVENTION

It is an object of the present invention to provide a photochemical method of immobilizing a desired ligand on a carbon-containing material surface which method does not suffer from the drawbacks described above.

A particular object of the invention is to provide a photochemical method which can be used generally to immobilize ligands on carbon-containing material surfaces.

Another particular object is to provide a photochemical method of immobilizing a ligand on a carbon-containing material surface which method is easier and less expensive to carry out and control, and which method is optimally faster than the known methods.

A further object of the present invention is to provide a photochemical method of immobilizing ligands on carbon-containing material surfaces, where the ligands are not subjected to damaging treatments and therefore substantially maintain their functions, even when the ligands are sensitive biomolecules.

This object is achieved by providing a method of immobilizing a ligand (L) to the surface (P) of a carbon-containing substrate material; said method comprising:

a photochemical step of linking of one or more ligand (L) via one or more photochemically reactive compounds (Q) to a carbon-containing material surface (P);

said carbon-containing material surface (P) being linked to the photochemically reactive compound (Q) either directly or via one or more spacers ($S_1$); and said photochemically reactive compound (Q) being linked to one or more ligands (L) either directly or optionally via one or more spacers (S) and/or thermochemically reactive compounds (T);

said spacers ($S_1$) and (S) being, equal or different, thermochemically or photochemically reactive or non-reactive spacers;

wherein the photochemically reactive compound (Q) is a quinone compound selected from the group consisting of monomeric quinone compounds, dimeric quinone compounds, and symmetrical or asymmetrical oligomeric quinone compounds;

said quinone compound (Q) containing a cyclic hydrocarbon, or from 2 to 10 fused cyclic hydrocarbons, said quinone compound having at least two conjugated carbonyl groups, the number of which does not exceeding twice the number of fused cyclic hydrocarbons;

said quinone compound (Q) optionally being substituted with substituents (R) which do not result in steric hindrance to the immobilization of the ligand (L) or do not disturb the photochemistry; and wherein the photochemical step comprises irradiation of the photochemically reactive compound (Q) with non-ionizing electromagnetic radiation having a wavelength in the range from UV to visible light, provided that said carbon-containing material does not consist of a nucleic acid probe.

The invention is based on the surprising finding that said quinone compounds as defined in claim 1 can be used as the photochemically reactive compound with very good results.

Quinone compounds are known as photochemically reactive compounds, but their use as photochemically reactive coupling compounds has never been suggested, even though there has been a rush in the development of new methods for immobilization of ligands to polymer surfaces.

Quinone Compounds

Quinone compounds are defined as compounds comprising at least 2 conjugated carbonyl groups placed in at least one cyclic hydrocarbon structure. Such compounds are well-known to a person skilled in the art.

The quinones suitable for use in the method according to the present invention are quinone, quinone dimers or oligomers of quinones, the latter having symmetrical or asymmetrical bonded quinones.

The quinone compound contains a cyclic hydrocarbon, or from 2 to 10 fused cyclic hydrocarbons, having at least two conjugated carbonyl groups. The number of carbonyl groups does not exceed twice the number of fused cyclic hydrocarbons.

The cyclic hydrocarbons may be fused in any position isomer.

The quinone compound is optionally being substituted with substituents (R) which do not result in steric hindrance to the immobilization of the ligand (L) or do not disturb the photochemistry, e.g. that the substituent has a chromophore which inhibits the activation of the quinone, e.g. by fluorescence, phosphorescence, radiation less transition, etc.

The cyclic hydrocarbons may independently of each other be of any ring size but are preferentially 5, 6, 10, 14, 18 carbon atom-membered aromatic rings which independently of each other may comprise one or several hetero atoms selected among —N—, —NH—, and —O—. The conjugated carbonyl groups may be located in any of these rings in any position provided that the quinoid structure is maintained.

Applicable Basic Quinone Compounds

Illustrations of applicable basic quinone compounds are shown in FIG. 1, wherein the compounds I–XXXVI may be substituted with one or more of the substituents R defined below.

Particularly Preferred Quinones

Particularly preferred quinones are claimed in claims 3 and 4.

In the preferred embodiment having the general formulas (XXXVII), (XXXVIII), and (XXXIX), also shown in FIG. 2, the letters m, n and o designate 0 or integers from 1–8, the sum of m, n and o being 8 or less; l indicates 0 or an integer from 1 to two times n; r and q indicate 0, 1 or 2; k indicates 0 or an integer from 1 to 2 times m; and t indicates 0 or an integer from 1 to 2 times o.

It is preferred that the sum of m, n and o is 8 or less.

R designates substituents as defined below.

The substituents are selected independently of each other. Preferably the total sum of the number of substituents (1+r+k+q+t) is less than the number of fused cyclic hydrocarbon compounds.

Specifically preferred quinones are selected from the group consisting of:

anthraquinones (V, VI, VII, X, XI, XIII, XXVIII), phenanthrenequinones (VIII, IX, XII), benzoquinones (I, II), naphthoquinones (III, IV, XXVII), and compound (XXVI, XXIX), particularly anthraquinones, phenanthrenequinones, and compound (XXVI).

Substituents R

The choice of substituents are important in controlling the solubility of the quinone and the overall affinity of the quinone towards the material surface; e.g. introduction of charged substituents will enhance the solubility in water and also increase or decrease the affinity towards charged material surfaces via attractive or repulsive ionic interactions. Thus, the substituents R may be selected in relation to the optimal hydrophobic/hydrophilic character which depends on the system and the solvent in which the photoreactive step takes place. Optimally, the quinone compound is partly soluble in the solvent.

The quinones are preferably substituted with a number of substituents which are less than three times the number of fused cyclic hydrocarbons, but they may, however, be completely saturated with substituents, provided that the quinoid structure is maintained.

Specifically the substituents (R) can themselves be quinones.

The useful substituents R may independently of each other be selected among the group consisting of:

functional groups comprising $-NO_2$, $-SO_3^-$, $-SO_2^-$, $-CN$, $-PO_3^{2-}$, $-PO_2^-$, $-COOH$, halogen, i.e. $-F$, $-Cl$, $-Br$, $-I$, primary amines, secondary amines and tertiary amines, or derivatives thereof; and hydrocarbyls which may be substituted with: $-NO_2$, $-SO_3^-$, $-CN$, $-PO_3^{2-}$, $-PO_2^-$, $-COOH$, halogen, i.e $-F$, $-Cl$, $-Br$, $-I$, epoxide, and $-H$;

said hydrocarbyls comprising alkyl having from 1–30 C-atoms, alkenyl having from 1–30 C-atoms, alkynyl having from 1–30 C-atoms, aryl having from 6–50 C-atoms, preferably 6–18 C-atoms, and derivatives thereof comprising combinations of these with equal or different substituents for the functional groups defined above; and said hydrocarbyl being straight/branched-chained, symmetric/asymmetric, chiral/achiral; containing one or more heteroatoms selected from the group consisting of $-N-$, $-NH-$, and $-O-$; or being fused, aromatic systems;

said fused, aromatic system containing one or more heteroatoms being heterocyclyl selected from the group consisting of pyridyl, imidazoyl, pyrimidinyl, pyridazinyl, quinolyl, acridinyl, imidazolyl, pyrrolyl, furyl, isoxazolyl, oxazolyl, which may be bound and/or fused in any position, and derivatives thereof comprising combinations of these with equal or different substituents as for the functional groups defined above.

Preferred substituents R are selected from the group consisting of: functional groups comprising $-NO_2$, $-SO_3^-$, $-SO_2^-$, $-CN$, $-PO_3^{2-}$, $-PO_2^-$, $-COOH$, halogen, i.e. $-F$, $-Cl$, $-Br$, $-I$, primary amines, secondary amines and tertiary amines, or derivatives thereof; and hydrocarbyls which may be substituted with: $-NO_2$, $-SO_3^-$, $-CN$, $-PO_3^{2-}$, $-PO_2^-$, $-COOH$, halogen, i.e $-F$, $-Cl$, $-Br$, $-I$, epoxide, and $-H$.

Preferred alkyls are methyl, ethyl, propyl, butyl, pentyl, hexyl, heptyl, octyl, nonyl, decanyl, undecanyl, dodecanyl, tridecanyl, tetradecanyl, pentadecanyl, hexadecanyl, heptadecanyl, octadecanyl, nonadecanyl, eicocanyl, straight or branched, with one or more double or triple bonds.

Preferred aryls are phenyl, naphtyl, biphenyl, tolyl, benzyl, cumenyl, mesityl, xylyl, pentalenyl, indenyl.

Non-ionizing Electromagnetic Irradiation

The electromagnetic radiation is chosen in order to activate the quinones. It is a non-ionizing electromagnetic radiation having a wavelength in the range from UV to visible, preferably shorter than 700 nm.

Normally the electromagnetic radiation is selected with a band of wavelengths in the range from 15 to 50 nm around a center wavelength. This band of wavelengths is chosen in order to be able to activate the quinones with electromagnetic radiation providing maximal absorption of the quinone chromophores.

The UV-light has a wavelength from UV to visible in order to minimize the interaction of the light with functional groups and sensitive ligands or biomolecules covalently linked to the quinones, such groups typically sensitive to electromagnetic radiation having wavelengths shorter than UV, whereby they are destroyed. It is thus possible to select an electromagnetic radiation having a wavelength in the wide range of wavelength where the quinones absorb electromagnetic radiation which selected radiation specifically activates the photochemically active group of interest.

Besides the above-mentioned special absorption properties of quinones, the high efficiency in the photoinduced immobilization of ligands observed in this invention, can in part be explained by the fact that the reactive state of the quinone (n¶*) is obtained in a very high yield upon excitation in the whole absorbtion range.

Normally incoherent continuous light will be chosen to activate the photoprobes. But the application of more complicated light sources such as monochromatic, polarized, pulsed or coherent light can be used.

In the examples described later on, a HPA lamp from Philips was used as light emitting source. Such HPA lamps are tubular medium-pressure metal halide lamps with iron and cobalt additives.

The lamps emit non-ionizing UV-light from 250 to 400 nm (corresponding to long-wave UV-A and UV-B, mainly 300–400 nm), and visible light from 400 to 700 nm, which makes the lamps suitable for use in the present method.

Irradiation times are selected in order to obtain a sufficient yield without degradating the immobilized ligand (L) or the carbon-containing material surface (P). The irradiation time is generally shorter than 12 hours, preferably less than 200 minutes, more preferably less than 60 minutes, most preferably less than 30 minutes.

Ligands

A ligand (L) is defined as a surface modifying compound which after immobilization to the polymer surface provides the polymer surface with a new surface characteristic.

The ligand (L) can be a functional group such as:
$-COOH$ (carboxylic acids), sulfonic acid derivatives, $-COOR$ (esters, including active esters), $-COX$ (acid halides, acid fluorids and acid chlorides, acid azides or similar active carboxylic acid derivatives), $-CONHNH_2$ (acid hydrazides), $-NHCONHNH_2$ (semicarbazides), $-NHCSNHNH_2$ (thiosemicarbazides), $-CN$ (nitriles), $-CHO$ (aldehydes), RR'CO (ketons), $-OH$ (alcohols), $-SH$ (thioles), $-SSR$ (disulfides), $-NH_2$ (amines, including primary, secondary and tertiary amines), $-NHNH_2$ (hydrazines), $-OR$ (ethers), epoxides, $-SR$ (sulfides), $-X$ (halides: fluoride, chloride, bromide, or iodide), $-NO_2$, $-CH_3$. Also, the ligand can be a biologically active molecule, such as biotin, toxins, herbicides, pesticides, carbohydrates, antibiotics (e.g. penicillins and other drugs, e.g. cell poisons), steroids, peptides, nucleotides, peptide nucleic acids (PNA) and nucleic acid binding partners, proteins and haptenes, functional groups (or derivatives thereof) or non-functional groups, such as methyl, ethyl, isobutyl, tertbutyl or aromates. These non-functional groups may e.g. be used to improve the biocompatibility of contact lenses, implants, etc.

Spacer

The spacers ($S_1$) or (S) are generally chosen with respect to length, flexibility, hydrophobic/hydrophilic character for each specific new surface characteristic.

The spacer ($S_1$) or (S) is as a thermochemically or photochemically non-active distance making compound.

Optionally, the ligand is linked to the polymer surfaces via a spacer, the only function of which is to make space between the two and thereby make the immobilization easier, particularly when the ligand is a large molecule. The spacer also provides for more ligands to be immobilized on the polymer surface.

The length of the spacer is selected for the specific purpose. Generally, the length is less than or about 400 Å. In some applications, preferably less than about 100 Å. In case of longer lengths of the spacer it is preferred to link more ligands to each spacer unit.

The spacer is also selected with respect to its hydrophobic/hydrophilic character. If e.g. the spacer links the quinone to the ligand before the photoreaction to the polymer, it is very important to optimize the hydrophobic/hydrophilic character of the total Q-S-L molecule in order to obtain optimal reaction conditions also depending on the solvent in the photoreactive step.

Examples of spacers are $C_1$–$C_{20}$ alkyl groups, e.g. polymethylene, optionally containing aromatic or mono/polyunsaturated hydrocarbons, polyoxyethylene such as polyethylene glycol, oligo/polyamides such as poly-β-alanine, polyglycine, polylysine, peptides in general, etc., oligosaccharides, oligo/polyphosphates such as phospho-mono/diesters, mono/diamides, etc., oligo/polysulfonic amides/esters. Moreover, the spacer may consist of combined units of the aforementioned or combined units thereof.

The importance of optimizing the spacer length and other properties are clearly illustrated in example 3 in which the photochemical grafting of primary amino groups is detected by the following thermochemical coupling of biotin and detection of the immobilized biotin with avidin. In this example a stepwise elongation of the spacer with β-alanine units was used. The oligoamide nature of the spacer allowed the easy synthesis of each compound using standard amide bond forming reactions and standard protecting group and deprotection schemes. In contrast to e.g. a simple aliphatic carbon spacer the oligoamide spacer is rather rigid due to the hindered rotation around the amide bonds and rather hydrophilic—but neutral—due to the ability of each amide bond to act both as donor and acceptor of hydrogen bonds. The optimum spacer length for this particular purpose was found to be anthraquinone amine compound 9. Increasing the spacer length with one more β-alanine unit did not increase the signal, but indicated a small decrease of signal (data not shown). This optimization of the spacer length for the biotin-avidin system is consistent with reports in the literature (see e.g. F. Kohnen et al., Complementary Immunoassays, page 62 (W. P. Collins ed.) John Wiley & Sons, New York, 1988).

Thermochemical Reactive Groups

Thermochemical reactive groups (T) are well-known in the art and are defined as functional groups, which are able to form covalent bonds to polymer surfaces (P) or ligands (L) under conditions in which the photochemically reactive group is non-reactive.

The thermochemical reactive groups may be —COOH (carboxylic acids), sulfonic acid derivatives, —COOR (esters, comprising active esters), —COX (acid halides, acid azides and similar carboxylic acid derivatives), —CONHNH$_2$ (acid hydrazides), —NHCONHNH$_2$ (semicar-bazides), —NHCSNHNH$_2$ (thiosemicarbazides), —CHO (aldehydes), RR'CO (ketones), —OH (alcohols), —X (halides: chloride, bromide, iodide), —SH (thioles), —SSR (disulfides), —NH$_2$ (amines, comprising primary, secondary and tertiary amines), —NHNH$_2$ (hydrazines), epoxides, maleimides.

One of the major advantages in this invention is the chemical stability of the quinone compounds. Thus, thermochemically reactive groups will not react with the quinones.

This is illustrated in synthesis of antraquinone acid hydrazide (compound 12, example 1) and antraquinone thiosemicarbazide (compound 15, example 1). Using benzophenones as the photochemically reactive group, the synthesis of such compounds would be impossible, as the acid hydrazide or thiosemicarbazide would condensate with the carbonyl group in the benzophenone, giving either cyclic compounds or oligomers.

Carbon-containing Material Surface

It is preferred that the carbon-containing material surface is a polymer surface.

The polymer may be any kind of polymer. Particularly preferred polymers are selected from the group consisting of: synthetic and natural polymers such as polystyrene, polyethylene, polyvinylacetate, polyvinylchloride, polyvinylpyrrolidone, polyacrylonitrile, polymethylmethacrylate, polytetrafluoroethylene, polycarbonate, poly-4-methylpentylene, polyester, polypropylene, cellulose, nitrocellulose, starch, polysaccharides, natural rubber, butyl rubber, styrene butadiene rubber, silicone rubber.

Also, the carbon-containing material can be selected from the group consisting of: premodified materials including silica, glass, control-led pore glass, silica gel, or metal which materials have been premodified to contain carbon; monolayer or multilayer films; Langmuir-Blodgett-films; micelles; biological membranes; proteins; nucleotides, peptide nucleic acids (PNA) and nucleic acid binding partners, natural or synthetic polymers coated with biological or organic material.

The polymer surfaces may e.g. be premodified by e.g. a corona treatment, a treatment of γ-lightening and silylation. Such treatment may enhance the reactiveness of the polymer and/or modify the hydrophobic or hydrophilic character of the surface.

The carbon-containing material may also be a silica, a glass, a controlled pore glass and a silica gel, or a metal which has been premodified to contain carbon, e.g. by silylation so as to make the surface able to form covalent bonds to other compounds, i.e. a quinone compound or a thermochemically reactive compound.

In the following the carbon-containing material surface is described as the "polymer surface" or "substrate". However, it is to be understood that the above-mentioned non-polymer surfaces may be treated as well.

Preferred Methods of Preparation

Preferred methods of carrying out the invention are defined in claims 11–16, wherein the respective compounds are linked to each other in a number of different ways.

A person skilled in the art will know that the method can be carried out in many other ways within the scope of the invention.

Preferred and illustrative embodiments (a)–(f) of the invention comprise the following reaction steps:

| | | |
|---|---|---|
| a) | Step 1: Q + L → Q-L | |
| | Step 2: Q—L + P → P—Q-L | (Photoreactive step) |
| b) | Step 1: Q + S → Q-S | |
| | Step 2: Q-S + L → Q-S-L | |
| | Step 3: Q-S-L + P → P—Q—S—L | (Photoreactive step) |
| c) | Step 1: P + Q → P-Q | ((Photoreactive step)) |
| | Step 2: P-Q + L → P-Q-L | ↓ |
| d) | Step 1: P + S$_1$ → P-S$_1$ | |
| | Step 2: P-S$_1$ + Q → P-S$_1$-Q | (Photoreactive step) |
| | Step 3: P-S$_1$-Q + L → P-S$_1$-Q-L | ↓ |
| e) | Step 1: Q + T → Q-T | |

-continued

| | |
|---|---|
| Step 2: Q-T + P → P-Q-T | (Photoreactive step) |
| Step 3: P-Q-T + L → P-Q-T-L | |
| f) Step 1: Q + S → Q-S | |
| Step 2: Q-S + T → Q-S-T | |
| Step 3: Q-S-T + P → P-Q-S-T | (Photoreactive step) |
| Step 4: P-Q-S-T + L → P-Q-S-T-L | |

In embodiment (f) the reaction order of S and T may be reversed in the steps 1 and 2.

Photoreactive Step

The photoreactive step can be carried out as described under Examples, and the thermochemical reactions can be carried out using standard synthetic procedures as known to a person skilled in the art.

Quinone-ligand Linking

Q may be linked to L by any synthetic methods of linking similar compounds. The bond obtained is preferably a covalent bond such as a C—C bond, a bond through acid derivatives (e.g. ester, amide, etc.), an ether bond, an amine, a sulfide or a disulfide bond. The reaction is carried out in a suitable solvent. After completed reaction, the solvent may be removed by e.g.. evaporation, decantation or filtration, or the solvent may be replaced by another solvent which is more suitable for the following photoreaction, where Q-L is linked to P. This reaction is preferably carried out in an aqueous solvent, where Q-L is brought into contact with P. The ligand L may have to be protected with one or more protecting groups during the photoreaction. The protecting groups can be selected so as to mask the sensitive functionalities of the ligand during the photochemical step, and so that the ligand can become unmasked in a subsequent step after the photoimmobilization.

The solvent is optimally the same in all steps of coupling of the compounds.

Covalent Bonding

The reaction involved in forming the covalent bonds may be selected among the standard synthetic procedures known to a skilled person, e.g. standard organic synthesis, peptide synthesis, oligonucletide synthesis and related areas. When using intermediates having multiple functional groups suitable semipermanent and/or transient protecting groups can be chosen to mask selected functional groups, thereby allowing regioselective synthesis of the Q-L and Q-S-L molecule. For well known techniques of protecting functionalities see T. W. Greene and P. G. M. Wuts, "Protective Groups in Organic Synthesis", John Wiley & Sons, New York, 1991.

Illustrative synthesis og Q-L and Q-S-L molecules, including selection of bond forming reactions and selection of suitable protective groups are illustrated in example 1.

Solvent

The solvent used in the photochemical step is preferably an aqueous medium or an aqueous medium containing up to 10% v/v of organic solvent, preferably up to 5% v/v of organic solvent. Neat organic solvent such as tetrachlormethane and benzene may be used. However, some organic solvent may cause problems because of its reactivity with e.g. the excited quinone. Also, organic solvents are more expensive and may result in environmental problems.

The solution in contact with the polymer is then exposed to light and irradiation is performed, optionally for a period up to 200 minutes, typically for less than 60 minutes, preferably less than 30 minutes. This modification does not change the physical properties of the polymer (stability, strength, transparency, etc.). The solution, preferably an aqueous solution, in which the covalent coupling takes place, is often buffered. This is done to keep defined pH during the reaction and to secure that certain groups are ionic. The pH value is preferably in the range from 0–7 or in the range 7–12. The optimal pH value is highly dependent on the specific reaction and the compounds involved. When amines are coupled, the pH is preferably less than 8 to protonate the amino functionality. By doing this, the reagent will be readily soluble in water and together with the quinone in the other part of the compound, the reagent as a whole acts as a soap. This means that the lipophilic quinone part will stick to the polymer, and the polar amino group will point out in the solvent. When e.g. carboxy groups are to be immobilized, the pH will preferably be more than 6 to obtain the same effect. When using aqueous systems, this differential polarity of the reagent as a whole is important in the photochemical immobilization.

Further Advantages

Contrary to benzophenones, the special redox properties of quinones, enables overall reduced quinones which can be formed during photolysis and which are not covalently linked to the surface to be "recycled" as illustrated in FIG. 3.

This recycling system increases the efficiency of the overall photochemical coupling. The high efficiency of the method according to the invention and the surprising findings that quinone-ligand conjugates can be photochemically immobilized on different polymers can be partly explained by this interesting recycling and "conservation" of photoprobes (the photochemical compounds which are to be subjected to a photochemical reaction).

As mentioned above, exited quinones react in radical reactions. The initial step is in general hydrogen atom abstraction and the rate of reaction is determined by the bond energy of the covalent bond between the hydrogen and the carbon to which it is bonded. This reaction mechanism has the consequence that the exited quinones are not able to react with water which has about the strongest binding of hydrogen atoms. Therefore, by using water as the solvent it is possible to generate extremely reactive species which are not able to react with the solvent.

Preferred Uses

Preferred uses of the carbon-containing material as prepared according to the method of this invention comprise use in a detection system, use as carrier for solid phase immuno assays, particularly as well as plates, test particles such as beads and micro spheres, test tubes, test sticks, and test strips, and use as a carrier for solid phase synthesis of peptides, oligonucleotides, carbohydrates and small organic molecules.

DETAILED DESCRIPTION

Prior Art—Photochemical Reaction of Arylazides

Figure 4:
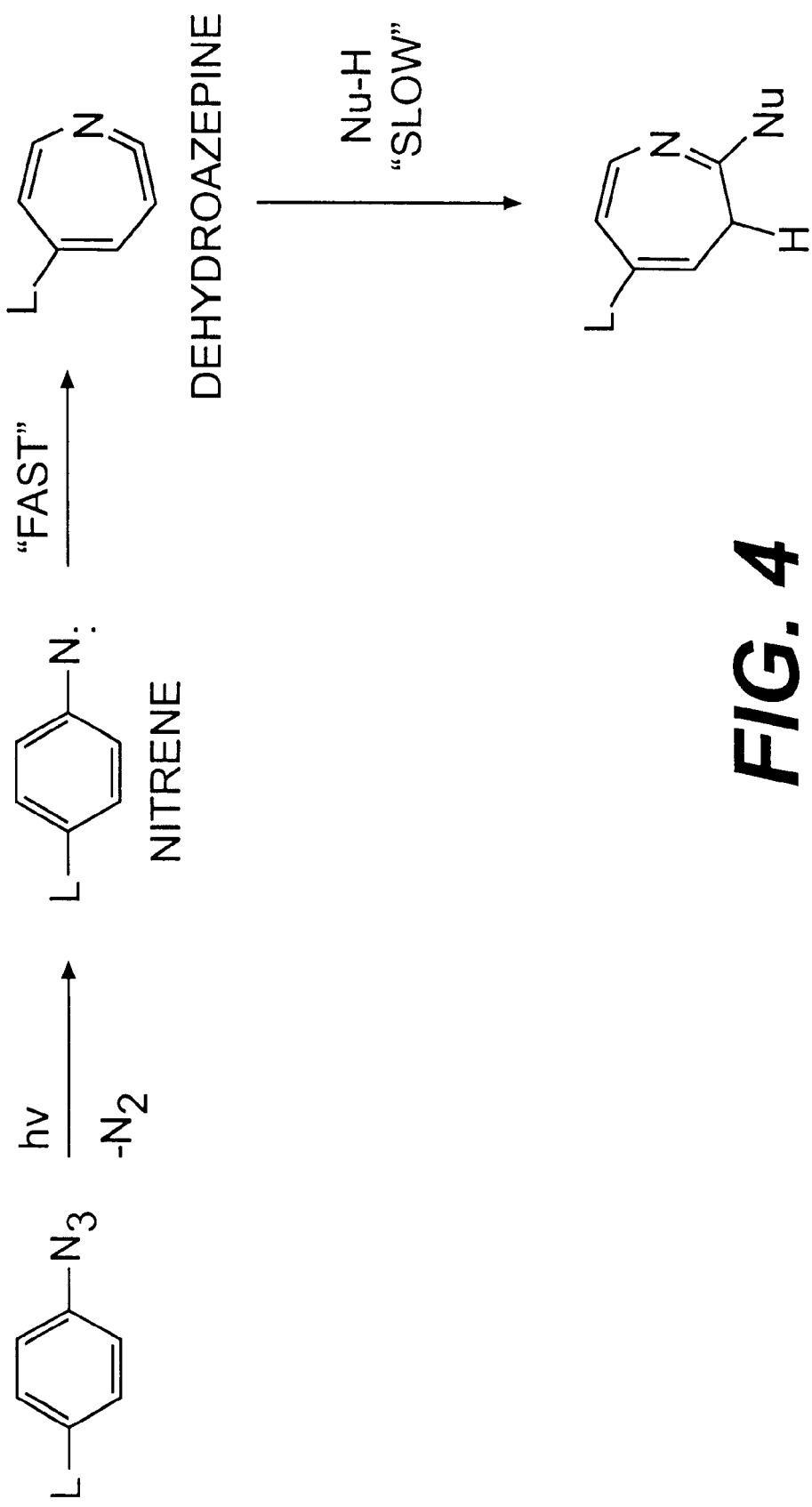
FIG. 4 illustrates the photochemical reaction of arylazides.

The photochemical reaction of the arylazides and derivatives thereof is illustrated in FIG. 4. Nu—H is e.g. $H_2O$ is R—OH, R—SH, R—$NH_2$ or "polymer". When irradiated with high energy UV light, i.e. as in Table 1 in example 2, a very reactive nitrene is formed and is quickly rearranged to a dehydroazepine. The latter is extremely unstable and will immediately react with the first nucleophilic compound it meets. If this is the solvent, e.g. water, the photoreagent is lost and no reaction is performed with the polymer. When using such reagents, it is therefore necessary that the surface is preincubated with the photoreagent, whereafter the redundant of the reagent is removed and the surface dried prior to the photolysis. When introducing strongly electron withdrawing groups the photochemical mechanism can be changed to nitrene photochemical reaction, but the nitrene compound will also react with the solvent, including water. Combined with long irradiation times (typically 12 hours), this makes the application of this photoreactive group time-consuming and inefficient.

Prior Art—Photochemical Reaction of Ketones

The major drawback of photochemical reactive ketones is their photochemical oxidation to the corresponding alcohol resulting in loss of the photochemical reagent. Also, they require long irradiation times of typically 12 hours which makes them unsuitable for immobilization of sensitive bio-molecules.

Prior Art—Photochemical Reaction of Benzophenone

The photochemistry of benzophenones results in the formation of a C—C bonding contrary to quinones which may form an ether bonding. Both groups have the advantage of not being reactive with water. Therefore, water can be used as a solvent.

Figure 5:
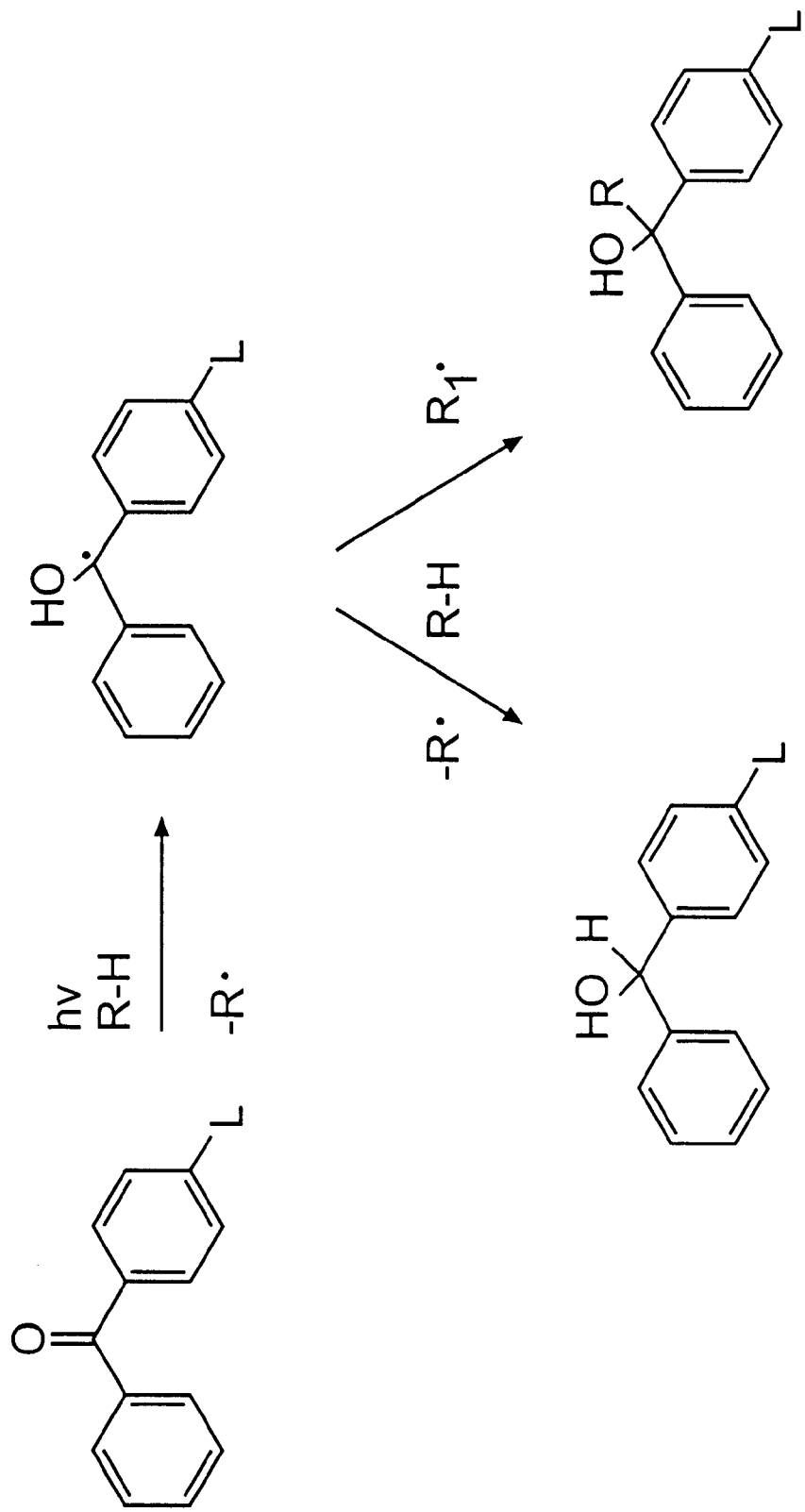
FIG. 5 illustrates the photochemical reaction of benzophenone.

The photochemical reaction of benzophenone and derivatives thereof is illustrated in FIG. 5, wherein R designates the polymer.

Such a photoreactive group based on benzophenone forms a radical by excitation with high energy UV light followed by hydrogen atom abstraction from a substrate, which radical either combines with the formed substrate radical to the product or which radical abstracts another hydrogen atom from a substrate, which results in a photochemical reduction to the corresponding alcohol with consequent loss of the photoreagent. Substrates for these reactions are organic molecules, including synthetic polymers, but also organic solvents such as e.g. alcohols.

The photochemical coupling typically requires irradiation at 320 nm for 12 hours to obtain an effective coupling to the polymer.

Photochemical Properties of Quinones of this Invention

Figure 6:
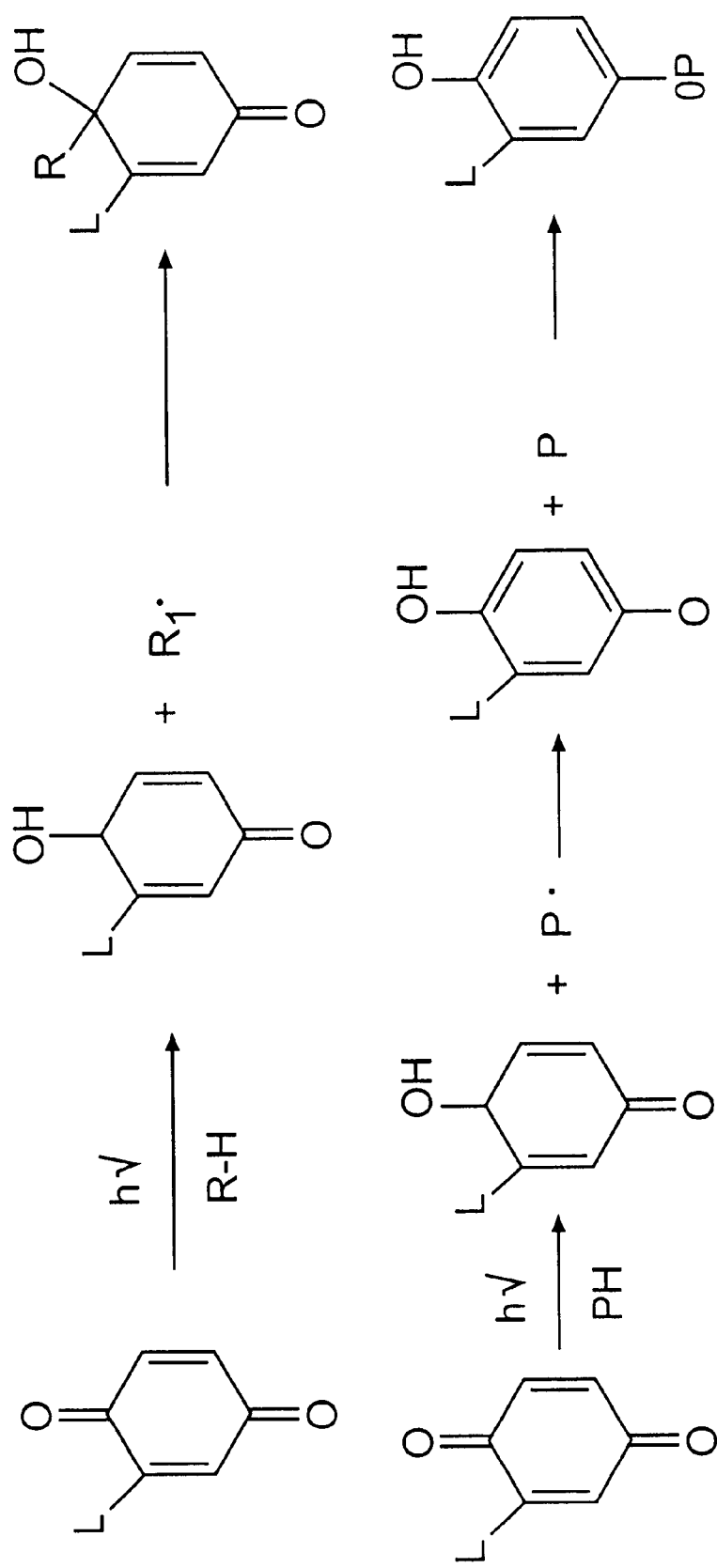
FIG. 6 illustrates photochemical properties of quinones of this invention.

The excited quinone reacts in general as a free radical and results in addition to double/triple bonds, abstracts hydrogen atoms, initiates chain reactions, etc. Due to the resonance configuration of the quinone, the radical reaction can take place on both or all the carbonyl groups of the quinone as illustrated in FIG. 6.

These reaction patterns are the fundamental photochemical properties of the quinones in this invention. Due to their general behaviour most quinones will be able to perform this kind of chemistry.

EXAMPLES

In the following the invention is further described by reference to a number of specific examples.
AQ: anthraquinone
BOP: benzotriazole-1-yl-N-oxytris-(dimethylamino)-phosphonium hexafluorophosphate
But: tert-butyl
DCC: dicyclohexylcarbodiimide
DCU: dicyclohexyl urea
DIEA: diisopropylethylamine
DMF: dimethylformamide
DMSO:. dimethylsulfoxide
EI: electron ionization
ELISA: enzyme linked immunosorbent assay
FAB: fast atom bombardment
Fmoc: fluorenylmethoxycarbonyl
HPLC: high performance liquid chromatography
Mp: melting poing
MS: mass spectrometry
NMR: nuclear magnetic resonance
NTA: N-nitrilotriacetic acid
OPD: phenylene-1,2-diamine dihydrochloride
PEG: polyethylene glycol
Pmc: 2,2,5,7,8 pentamethylchroman-6-sulfonyl
TFA: trifluoroacetic acid
THF: tetrahydrofuran
TLC: thin layer chromatography Example 1

Figure 7:
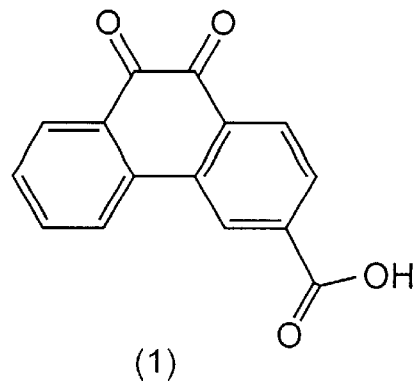
FIG. 7 shows quinone-ligand, quinone-spacer-ligand compounds nos. 1–22 prepared in example 1.
Figure 7:
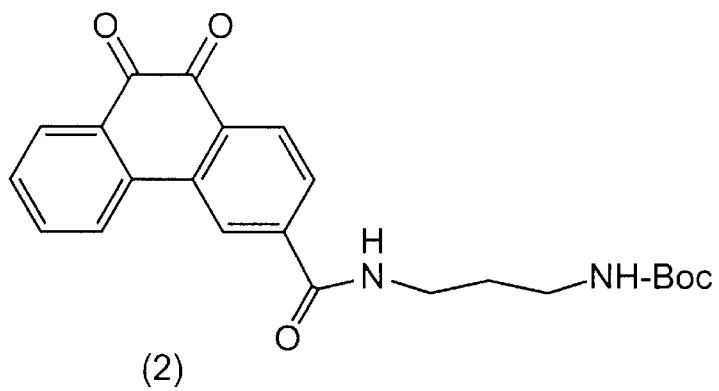
Figure 7:
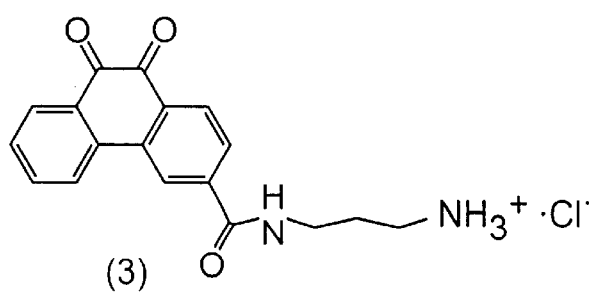
Figure 7:
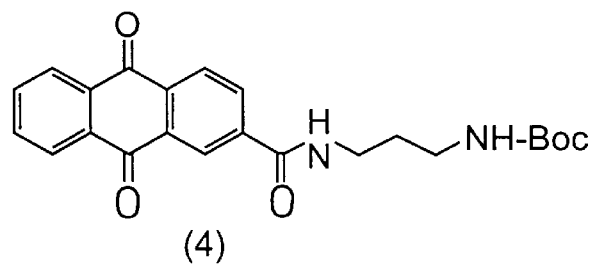
Figure 7:
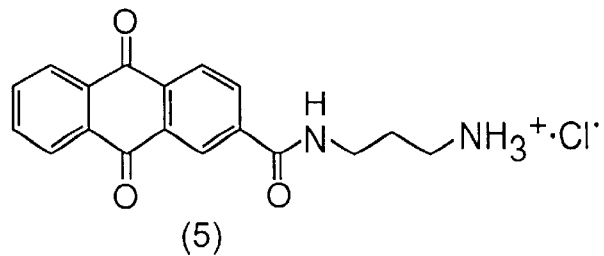
Figure 7:
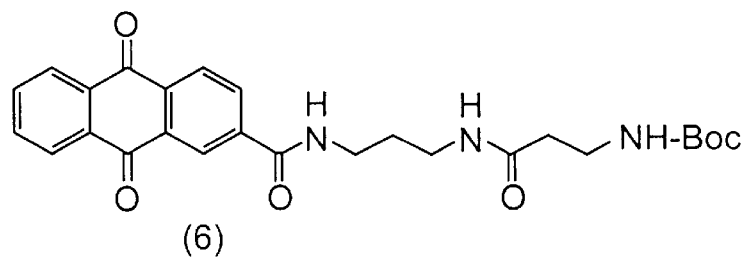
Figure 7:
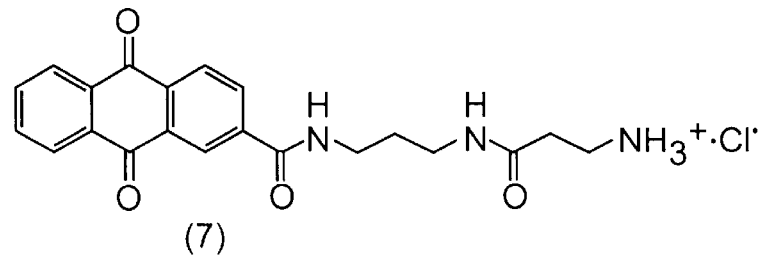
Figure 7:
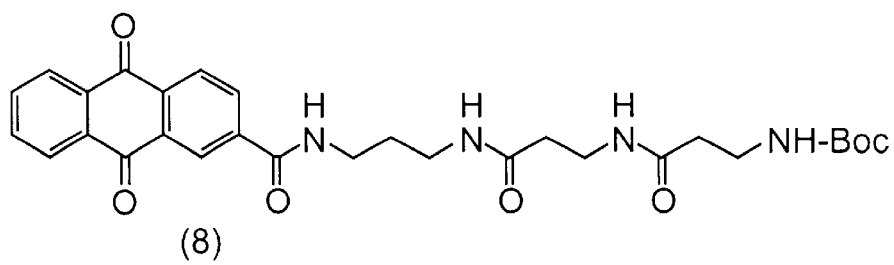
Figure 7:
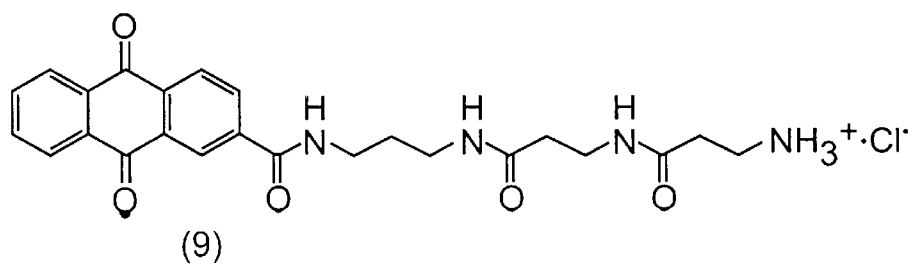
Figure 7:
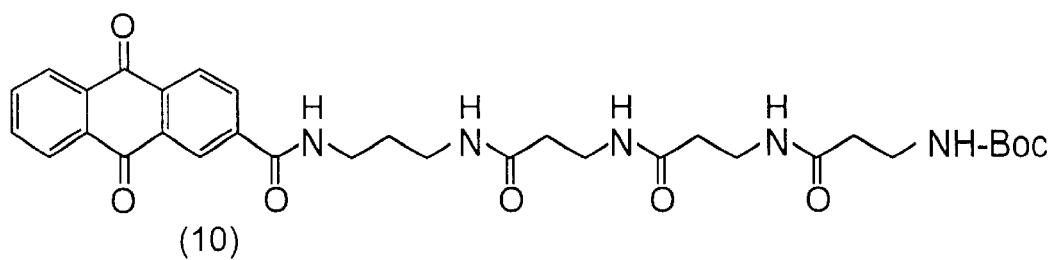
Figure 7:
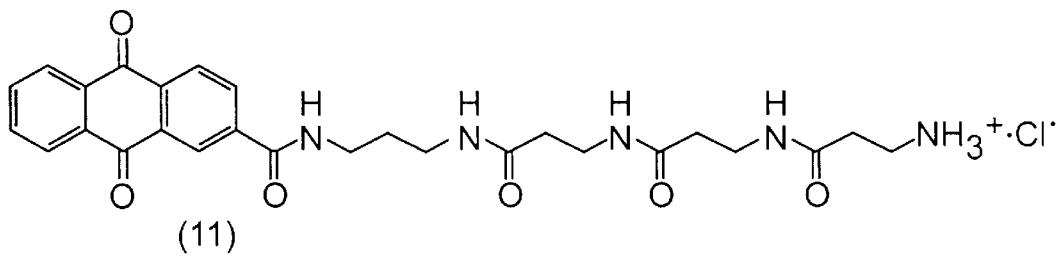
Figure 7:
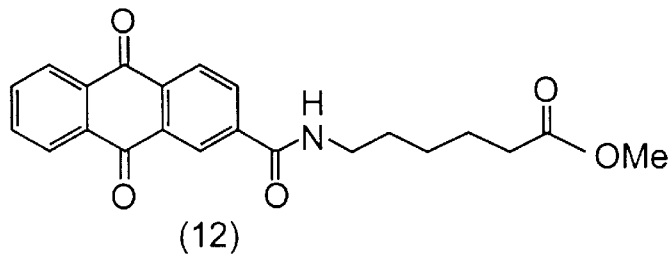
Figure 7:
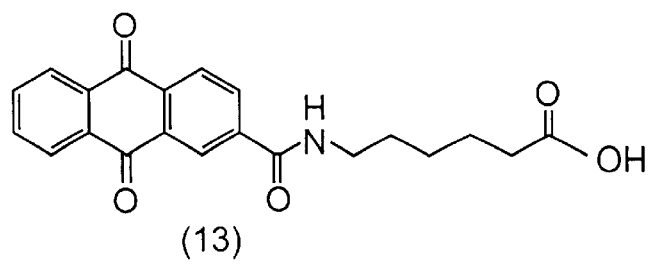
Figure 7:
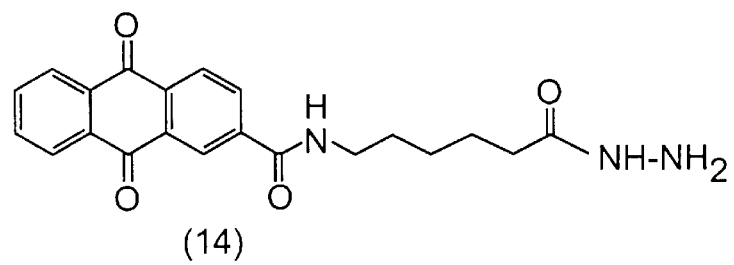
Figure 7:
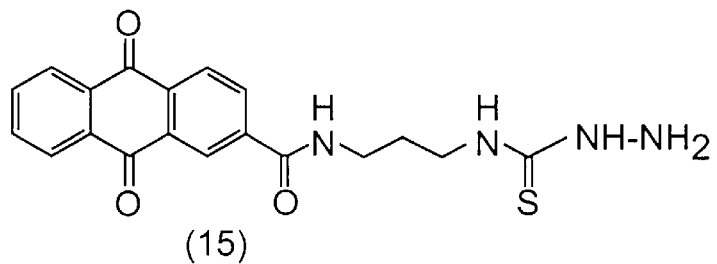
Figure 7:
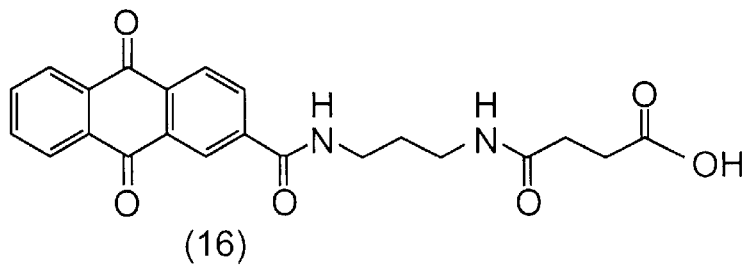
Figure 7:
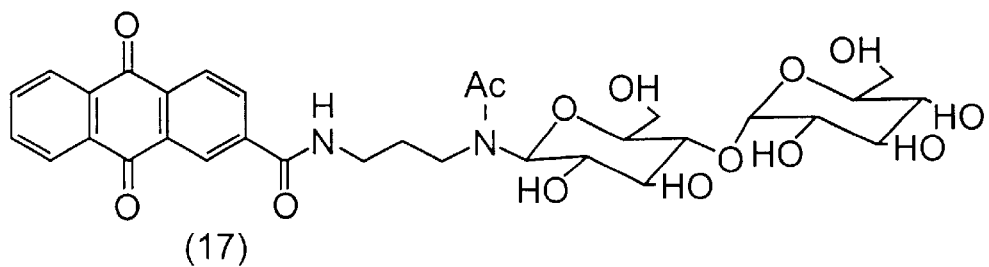
Figure 7:
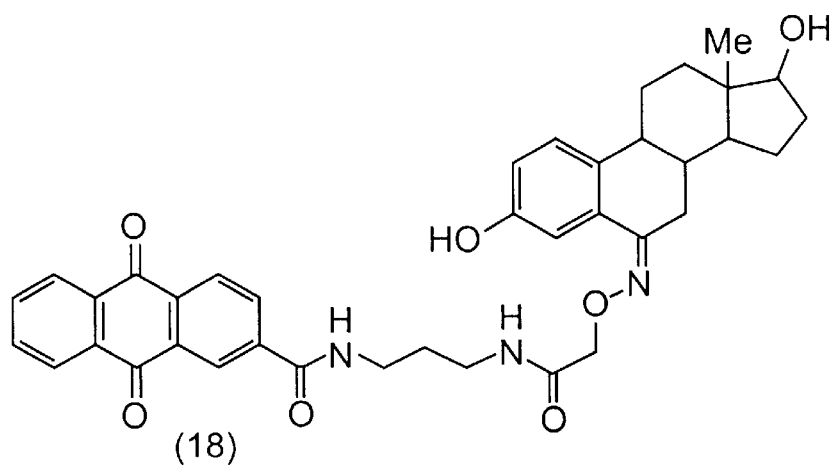
Figure 7:
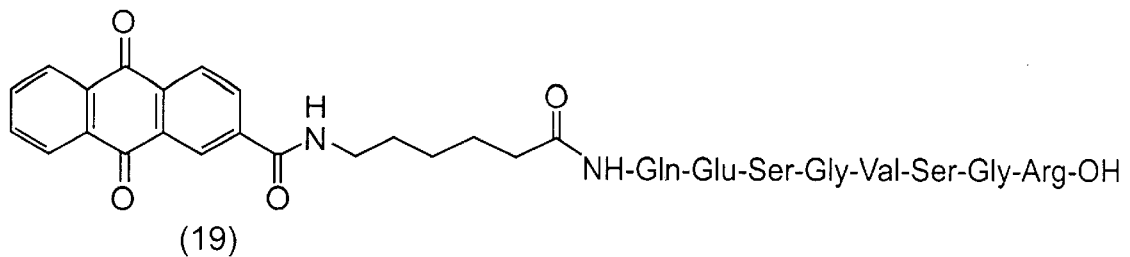
Figure 7:
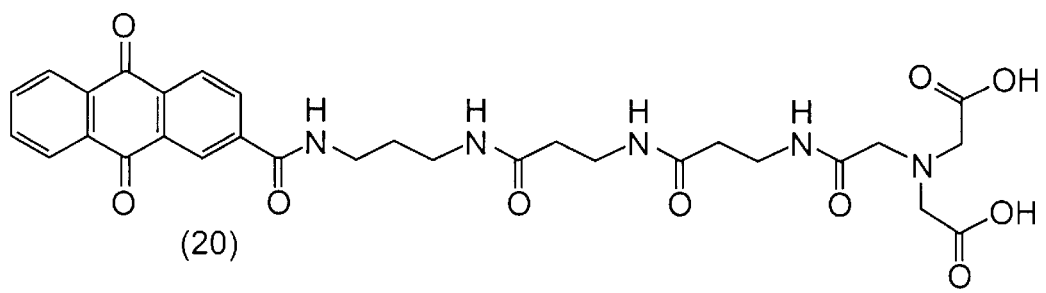
Figure 7:
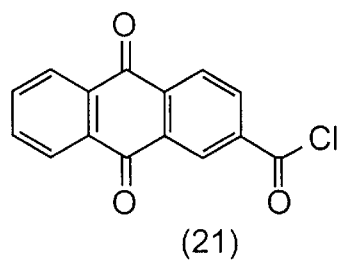
Figure 7:
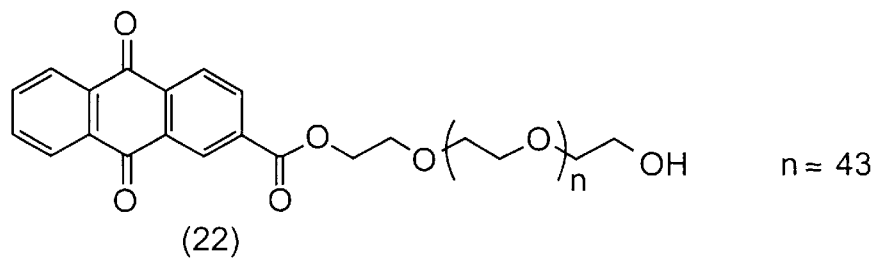

FIG. 7 shows quinone-ligand, quinone-spacer-ligand compounds nos. 1–22 which have been synthesized as described in the following.

The mono-Boc-protected diamines were prepared as described by Krapcho and Kuell, Synthetic Communications 1990, 20, 2559–2564.

3-Carboxy-phenanthrenequinone (Compound No. 1)

3-Acetylphenanthrene (5 g, 0.23 mmol) was dissolved in warm acetic acid (100 ml, 60 ° C.) and chrom(VI)oxide (30 g, 0.6 mol) was added in small portions. During this the temperature rose to the boiling point. After addition of all chrom(VI)oxide the solution was diluted with water (500 ml) and the precipitate was filtered off, washed with acetic acid/$H_2O$ (1:1), cold acetic acid and finally with diethyl ether. Yield: 2.1 g (37% from 3-acetylphenanthrene); Mp: 280° C.

MS (EI): 252 ($M^+$).

$^1H$ NMR ($d_6$-DMSO): 8.70 ppm (s, 1H), 8.34 (d, 1H), 8.08 (m, 3H), 7.80 (t, 1H), 7.57 (t, 1H).

N-(3-Boc-aminopropyl)-phenanthrenequinone-3-carboxamide (Compound No. 2)

Compound no. 1 (250 mg, 1.0 mmol), DCC (245 mg, 1.2 mmol) and HODhbt (178 mg, 1.1 mmol) were dissolved in dioxane (50 ml), and the mixture was allowed to react overnight. The dioxane was evaporated in vacuo, and the residue was suspended in DMF (25 ml). Mono-Boc-1,3-propanediamine.HCl (333 mg, 1.2 mmol) was added to the suspension followed by excess triethylamine (1 ml). After 1 hour DCU was filtered off and water (150 ml) was added. The yellow precipitate was collected by filtration and the product recrystallized from ethyl acetate. Yield: 0.235 mg (56% from compound no. 1); Mp: 195° C. (dec.).

$^1H$ NMR (CDCl$_3$): 8.02 ppm (t, 1H), 7.98 (s, 1H), 7.65 (d, 1H), 7.51–7.45 (m, 2H), 7.33 (d, 1H), 7.14 (t, 1H), 6.89 (t, 1H), 5.62 (b, 1H), 2.89–2.71 (m, 2H), 2.44–2.41 (m, 2H), 1.11–0.75 (m, 11H).

N-(3-Aminopropyl)-phenanthrenequinone-3-carboxamide.HCl (Compound No. 3)

Compound no. 2 (100 mg, 0.24 mmol) was dissolved in slightly warmed acetic acid (2.5 ml, 50° C.), and 1 M HCl in acetic acid was added (2.5 ml). After 5 minutes ether was added (10 ml), and the precipitate was collected by filtration and was washed several times with ether. Yield: 81 mg (95% from compound no. 2).

$^1H$ NMR ($d_6$-DMSO): 9.20 ppm (b, 1H), 8.78 (s, 1H), 8.54 (d, 1H), 8.14–7.99 (m, 6H), 7.86 (t, 1H), 7.60 (t, 1H), 3.38 (—$CH_2$—N—R), 2.88 (b, 2H), 1.69 (s, 2H).

UV (ethanol/water): $\lambda_{max}$=266 nm ($\epsilon$=39000), 330 (5700), 424 (1400).

N-(3-Boc-aminopropyl)-anthraquinone-2-carboxamide (Compound No. 4)

Anthraquinone-2-carboxylic acid (2.52 g 10 mmol) was suspended in dry THF (100 ml). The suspension was cooled to 0° C., and DCC (2.06 g, 10 mmol) was added, and the mixture stirred for 5 minutes. Solid HODhbt (1.63 g, 10 mmol) was added, and the mixture stirred for 10 minutes at 0° C. and then at room temperature overnight. THF was removed in vacuo (40° C.), and the solid residue was resuspended in DMF (100 ml). Mono-Boc-1,3-propanediamine.HCl (4.21 g, 20 mmol) was added to the suspension followed by excess triethylamine (7 ml). After 2 h DCU was removed by filtration and water (200 ml) was added. The yellow precipitate was collected by filtration and the product recrystallized from ethyl acetate (200 ml). Yield: 3.53 g (87% from anthraquinone-2-carboxylic acid); Mp: 173–175° C.; TLC (ethyl acetate): $R_f$=0.61.

MS (FAB$^+$): 409.1 (MH$^+$).

$^1H$ NMR ($d_6$-DMSO): 9.00 ppm (t 1H), 8.75 (s, 1H), 8.40 (dd, 1H), 8.30 (m, 3H), 8.05 (m, 2H), 6.90 (t, 1H), 3.40 (q, 2H), 3.10 (q, 2H), 1.80 (qn, 2H), 1.45 (s, 9H).

N-(3-Aminopropyl)-anthraquinone-2-carboxamide.HCl (Compound No. 5)

Compound no. 4 (5.92 g, 14.5 mmol) was suspended in methanol (200 ml). 6 M HCl in methanol (15 ml) was added, and the mixture was heated to reflux for 1 hour. The mixture was cooled to 0° C., and diethyl ether (200 ml) was added. The precipitated product was collected by filtration and washed several times with ether. Yield: 3.98 g (80% from compound no. 4); Mp: 250° C. (dec.); TLC (1-butanol/acetic acid/water 4:1:1): $R_f$=0.43.

MS (FAB$^+$): 309.1 (MH$^+$).

$^1H$ NMR ($d_6$-DMSO): 9.00 ppm (t, 1H), 8.75 (s, 1H), 8.50 (dd, 1H), 8.30 (m, 3H), 8.15 (s, 3H), 8.10 (m, 2H), 3.50 (q, 2H), 2.95 (t, 2H), 1.95 (qn, 2H).

UV (ethanol/water): $\lambda_{max}$=256 nm ($\epsilon$=49000), 332 (4700), 390 (310).

Boc-βAla-NH—(CH$_2$)$_3$—NHCO—AO (Compound No. 6)

Boc-β-Ala-OH (0.605 g, 3.20 mmol) and BOP (1.283 g, 2.9 mmol) were dissolved in DMF (50 ml), and triethylamine (4 ml, 30 mmol) was added. The mixture was allowed to preactivate for 5 minutes before compound no. 5 (1.00 g, 2.90 mmol) was added in one portion. The reaction mixture was stirred at room temperature overnight, and the product was precipitated by the addition of water (50 ml). The crude product was filtered off, washed several times with water, and finally recrystallized from ethanol/water. Yield: 1.40 g (92% from compound no. 5); Mp: 178–179° C., TLC (ethyl acetate/methanol/acetic acid 85:10:5): $R_f$=0.73. MS (FAB$^+$): 480.2 (MH$^+$).

$^1$H NMR (d$_6$-DMSO): 9.00 ppm (t, 1H), 8.75 (s, 1H), 8.40 (dd, 1H), 8.35 (m, 3H), 8.05 (m, 2H), 7.90 (t, 1H), 6.80 (t, 1H), 3.40 (q, 2H), 3.20 (q, 4H), 2.30 (t, 2H), 1.75 (qn, 2H), 1.45 (s, 9H).

H-βAla-NH—(CH$_2$)$_3$NHCO—AO.HCl (Compound No. 7)

Compound no. 6 (0.220 g 2.54 mmol) was suspended in methanol (40 ml). 6 M HCl in methanol (5 ml) was added, and the mixture was heated to reflux for 1 hour. The mixture was cooled to 0° C., and diethyl ether (40 ml) was added. The precipitated product was collected by filtration and washed several times with ether. Yield: 0.970 g (92% from compound no. 6); Mp: 219° C. (dec.); TLC (1-butanol/acetic acid/water 4:1:1): $R_f$: 0.40.

MS (FAB$^+$): 380.1 (MH$^+$).

$^1$H NMR (d$_6$-DMSO): 9.10 ppm (t, 1H), 8.75 (s, 1H), 8.45 (dd, 1H), 8.35 (m, 4H), 8.15 (s, 3H), 8.10 (m, 2H), 3.45 (m, 4H), 3.25 (q, 2H), 3.10 (t, 2H), 1.80 (q, 2H).

Boc-βAla-βAla-NH—(CH$_2$)$_3$—NHCO—AO (Compound No. 8)

Compound no. 7 (0.492 g, 2.60 mmol) and BOP (0.955 g, 2.16 mmol) were dissolved in DMF (80 ml), and triethylamine (1.5 ml, 10.8 mmol) was added. The mixture was allowed to preactivate for 5 minutes before compound no. 7 (0.900 g, 2.16 mmol) was added in one portion. The reaction mixture was stirred at room temperature overnight, and the product was precipitated by the addition of water (80 ml). The crude product was filtered off, washed several times with water, and finally recrystallized from ethanol/water. Yield: 0.740 g (62% from compound no. 7); Mp: 183–184° C.; TLC (ethyl acetate/methanol/acetic acid 85:10:5): $R_f$=0.45.

MS (FAB$^+$): 551.3 (MH$^+$).

$^1$H NMR (d$_6$-DMSO): 9.05 ppm (t, 1H), 8.75 (s, 1H), 8.30 (m, 4H), 8.10 (m, 2H), 7.90 (dt, 2H), 6.75 (t, 1H), 3.40 (q, 2H) 3.35 (q, 2H), 3.20 (dq, 4H), 2.30 (dt, 4H), 1.80 (qn, 2H), 1.45 (s, 9H).

H-βAla-βAla-NH—(CH$_2$)3—NHCO—AO.HCl (Compound No. 9)

Compound no. 8 (0.740 g, 1.35 mmol) was suspended in methanol (15 ml). 6 M HCl in methanol (1 ml) was added, and the mixture was heated to reflux for 1 hour. The mixture was cooled to 0° C., and diethyl ether (15 ml) was added. The precipitated product was collected by filtration and washed several times with ether. Yield: 0.591 g (90% from compound no. 6); Mp: 216–219° C.; TLC (1-butanol/acetic acid/water 4:1:1): $R_f$=0.26.

MS (FAB$^+$): 451.1 (MH$^+$).

$^1$H NMR (d$_6$-DMSO): 9.00 ppm (t, 1 h), 8.60 (d, 1H), 8.35 (dd, 1H), 8.30 (d, 1H), 8.25 (m, 2H), 8.15 (t, 1H), 7.95 (m, 3H), 7.80 (s, 3H), 3.30 (m, 6H), 3.15 (q, 2H), 2.50 (t, 2H), 2.30 (t, 2H), 1.75 (qn, 2H).

Boc-βAla-βAla-βAla-NH—(CH$_2$)$_3$—NHCO—AO (Compound No. 10)

Compound no. 9 (0.263 g, 1.39 mmol) and BOP (0.513 g, 1.16 mmol) were dissolved in DMF (50 ml), and diisopropylethyl amine (2 ml, 12 mmol) was added. The mixture was allowed to preactivate for 5 minutes before compound no. 9 (0.564 g, 1.16 mmol) was added in one portion. The reaction mixture was stirred at room temperature overnight, and the product was precipitated by the addition of water (50 ml). The crude product was filtered off, washed several times with water, and finally recrystallized from ethanol/water. Yield: 0.654 g (91% from compound no. 9); Mp: 209–213° C.; TLC (methanol): $R_f$=0.60. MS (FAB$^+$): 622.2 (MH$^+$).

$^1$H NMR (d$_6$-DMSO): 9.05 ppm (t, 1H), 8.75 (s, 1H), 8.30 (m, 4H), 8.10 (m, 2H), 8.00 (dt, 2H), 7.90 (t, 1H), 6.80 (t, 1H), 3.30 (dq, 6H), 3.20 (dq, 4H), 2.30 (tt, 6H), 1.80 (qn, 2H), 1.45 (s, 9H).

H-βAla-βAla-βAla-NH—(CH$_2$)$_3$—NHCO—AO.HCl (Compound No. 11)

Compound no. 10 (0.500 g, 0.800 mmol) was suspended in methanol (15 ml). 6 M HCl in methanol (1 ml) was added, and the mixture was heated to reflux for 1 hour. The mixture was cooled to 0° C., and diethyl ether (15 ml) was added. The precipitated product was collected by filtration and washed several times with ether. Yield: 0.400 g (89% from compound no. 10); Mp: 235–237° C. (dec.); TLC: (1-butanol/acetic acid/water 4:1:1): $R_f$0.14. MS (FAB$^+$): 522.1 (MH$^+$).

$^1$H NMR (d$_6$-DMSO): 9.00 ppm (t, 1H), 8.65 (d, 1H), 8.30 (d, 1H), 8.25 (m, 2H), 8.15 (t, 1H), 8.00 (m, 2H), 7.90 (s, 3H), 3.35 (t, 2H), 3.25 (q, 4H), 3.15 (q, 2H), 2.95 (q, 2H), 2.50 (t, 2H), 2.30 (dt, 4H), 1.70 (qn, 2H).

N-(5-carboxymethyl-pentyl)anthraquinone-2-carboxamide (Compound No. 12)

Anthraquinone-2-carboxylic acid (2.52 g, 10 mmol) was suspended in dry THF (100 ml) and cooled to 0° C. Then, DCC (2.26 g, 11 mmol) was added, and the mixture stirred for 5 minutes. Solid HODhbt (1.63 g, 10 mmol) and the mixture stirred at 0° C. for 10 minutes and then at room temperature overnight. THF was removed in vacuo, and the solid residue was resuspended in DMF (100 ml). 6-Aminohexanoic acid methyl ester.HCl (1.99 g, 11 mmol) followed by triethyl amine (7 ml, 50 mmol) were added, and the mixture stirred at room temperature overnight. DCU was removed by filtration, and the product was precipitated by the addition of water (200 ml). The crude product was collected by filtration and recrystallized from ethyl acetate. Yield: 3.09 g (73% from anthraquinone-2-carboxylic acid); Mp: 144–145° C.; TLC (ethyl acetate): $R_f$=0.68. MS (FAB$^+$): 380.1 (MH$^+$).

$^1$H NMR (d$_6$-DMSO): 9.00 ppm (t, 1H), 8.75 (s, 1H), 8.40 (dd, 1H), 8.30 (m, 3H), 8.05 (m, 2H), 3.70 (s, 3H), 3.40 (q, 2H), 2.40 (t, 2H), 1.70 (qn, 6H), 1.40 (qn, 4H).

N-(5-carboxypentyl)-anthraquinone-2-carboxamide (Compound No. 13)

Compound no. 12 (0.949 g, 2.5 mmol) was suspended in THF (15 ml). 0.5 M LiOH (15 ml) was added, and the mixture stirred at room temperature for 1 hour. THF was removed in vacuo, and the product was precipitated by the addition of 2 M HCl (6 ml). The crude product was collected by filtration, washed with water and dried in vacuo. Yield: 0.822 g (90% from compound no. 12); Mp: 198–199° C.; TLC (petroleum ether/ethyl acetate/acetic acid 5:5:1): $R_f$=0.43. MS (FAB$^+$): 366.2 (MH+).

$^1$H NMR (d$_6$-DMSO): 12.00 ppm (s, 1H), 9.00 (t, 1H), 8.75 (s, 1H), 8.40 (dd, 1H), 8.35 (m, 3H), 8.00 (m, 2H), 2.30 (t, 2H), 1.60 (qn, 6H), 1.40 (qn, 4H).

N-(6-hydrazido-hexyl)-anthraquinone-2-carboxamide (Compound No. 14)

Compound no. 12 (0.5 g, 1.32 mmol) was suspended in methanol (5 ml). Hydrazine hydrate (1 ml, 20 mmol) was added in one portion, and the reaction mixture was refluxed for 6 h and then allowed to cool to room temperature. The solvent was removed in vacuo, and the remanence was resuspended in ice cold water (20 ml). The precipitated product was collected by filtration and washed with water and dried in vacuo. Yield: 0.373 g (75% from compound no. 12); Mp: 181° C. (dec.); TLC (ethyl acetate/methanol 6:4): $R_f$=0.48. MS (FAB$^+$): 380.24 (MH$^+$).

1-(3-(carboxamido-anthraquinone-2-yl)-propyl)-thiosemicarrbazide (Compound 15)

BOP (0.257 g, 0.58 mmol) and carbon disulfide (0.35 ml, 5.8 mmol) was dissolved in DMF. Then, triethyl amine (0.24 ml, 1.74 mmol) followed by solid compound no. 5 (0.2 g, 0.58 mmol) was added. The mixture was stirred for 1 hour at room temperature. Excess carbon disulfide was removed in vacuo, and the solution was added dropwise to a stirred ice cold solution of hydrazine hydrate (0.5 ml, 7.8 mmol) in DMF (0.5 ml). The mixture was stirred overnight at room temperature, and the product was precipitated by addition of ice cold water (25 ml). The precipitated product was collected by filtration and washed with water and dried in vacuo. Yield: 0.164 g (74% from compound no. 5); Mp: 202–205° C. (dec.); TLC (ethyl acetate/methanol 6:4): $R_f$=0.63.

MS (FAB$^+$): 383.1 (MH$^+$).

$HO_2C—(CH_2)_3—CONH—(CH_2)_3—NHCO—AO$ (Compound No. 16)

Compound no. 12 (0.45 g, 1.31 mmol) and maleic anhydride (0.19 g, 1,9 mmol) was dissolved in DMF (30 ml). Triethylamine (1.8 ml, 13.1 mmol) was added, and the mixture was stirred at room temperature for 3 hours. The product was precipitated by the addition of ice cold 0.5 M HCl (30 ml), collected by filtration and recrystallized from ethanol/water. Yield: 0.374 g (79% from compound no. 12); TLC (ethyl acetate/methanol 6:4): $R_f$=0.33.

MS (FAB$^+$): 409.1 (MH$^+$).

α-D-Glcp-(1-∞4)-β-D-Glcp-1-N(Ac)-(CH$_2$)$_3$—NH—CO—AO (Compound No. 17)

Compound no. 5 (0.103 g, 0.300 mmol) and maltose monohydrate (0.324 mg, 0.900 mmol) were dissolved in dry methanol. DIEA (70 µl, 0.400 mmol) was added and the mixture was heated in nitrogen atmosphere overnight. The mixture was cooled to 0° C., and acetic anhydride (1 ml) was added. After standing at room temperature overnight methanol was removed in vacuo, and the residue was dissolved in water and filtered through a 0.2 µm filter and freeze dried. The resulting solid was redissolved in water and loaded onto two Sep-Pak Vac cartridges (C$_{18}$, 100 mg sorbent).

Residual free maltose was eluted with water (2×10 ml) and the quinone-maltose conjugate eluted with 50% acetonitrile/water. The combined acetonitrile/water fractions were freeze dried to yield compound no. 17 as a slightly yellow voluminous powder. Yield: 0.203 mg (100% from compound no. 5); TLC: $R_f$=0.32 (major spot, compound no. 17); $R_f$=0.66 (minor spot, CH$_3$—CONH—(CH$_2$)$_3$—NHCO—AQ); HPLC (Delta Pak 5µ C$_{18}$ 3.9×150 mm; buffer A: 0.1% TFA in H$_2$O; buffer B: 0.1% TFA in acetonitrile/water 9:1; gradient: 100% A for 2 minutes, then a linear gradient from 100% A to 100% B over 20 minutes, then 100% B for 5 minutes): Rt=12.07 minutes (77%, 332 nm), 12.29 (5%), 12.67 (14%), 13.35 (4%, CH$_3$—CONH—(CH$_2$)$_3$—NHCO—AQ).

MS (FAB$^+$): 675.25 (MH$^+$); 717.48 (MH$^+$+CH$_3$—CO); 759.58 (MH$^+$+2CH3CO); 351.16 (CH$_3$—CONH—(CH$_2$)$_3$—NHCO—AQ.H$^+$).

AO—CO—(CH$_2$)3—NH-6-ketoestradiol-6-(O-carboxymethyl)-oxime (Compound No. 18)

Compound no. 5 (48 mg, 0.139 mmol), 6-ketoestradiol-6-(O-carboxymethyl)-oxime (50 mg, 0.139 mmol) and BOP (65 mg, 0.139 mmol) were suspended in DMF. Diisopropylethyl amine (49 µl, 0.278 mmol) was added and the mixture stirred at room temperature for 3 hours. Water (3 ml) was added, and the precipitated product was filtered off, washed with 10% Na$_2$CO$_3$ (three times), 10% KHSO$_4$ (three times), several times with water and finally dried in vacuo. Yield: 90 mg (100%); TLC (ethyl acetate/acetic acid 95:5): $R_f$=0.27. MS (FAB$^+$): 650.26 (MH$^+$); 672.28 (M+Na$^+$).

AO—CO-εAhx-Gln-Glu-Ser-Gly-Val-Ser-Gly-Arg-OH (Compound No. 19)

H-Gln-Glu(OBu$^t$)-Ser(bu$^t$)-Gly-Val-Ser(bu$^t$)-Gly-Arg (Pmc)-PepSyn-KA was synthesized using a standard Fmoc-protocol on a custom-made fully automatic continuous flow peptide synthesizer with solid phase online monitoring of coupling reactions. Fmoc-Arg(Pmc)-PepSyn-KA resin (750 mg, 0.09 mmol/g) was loaded onto a column and each individual coupling was performed with the corresponding Fmoc-amino-acid-OPfp-esters (3 equivalents) and HODhbt (1 equivalent) added as catalyst/indicator except serine which was coupled as the Dhbt-ester. At the end of the synthesis the peptidyl resin was transferred to a bubbler apparatus and N-(5-carboxypentyl)-anthraquinone-2-carboxamide (compound no. 13) (3 equivalents) and BOP (3 equivalents) followed by DIEA (9 equivalents) added to the resin. The coupling was allowed to proceed overnight. The N-terminally quinone substituted peptide was cleaved from the resin with Reagent K (TFA/H$_2$O/thioanisole/phenol/ethane diethiol 82.5:5:5:2.5). The resin was filtered off on a sintered glass filter, washed several times with TFA, and the cleavage mixture concentrated in a stream of nitrogen. The peptide was precipitated with ice cold diethyl ether, and the peptide pellet was redissolved in 2% acetic acid/water, filtered through a 0.2 µm filter and finally freeze dried. HPLC (Delta Pak 5µ C$_{18}$ 3.9×150 mm; buffer A: 0.1% TFA in H$_2$O; buffer B: 0.1% TFA in acetonitrile/water 9:1; gradient: 100% A for 2 minutes, then a linear gradient from 100% A to 100% B over 20 minutes, then 100% B for 5 minutes): Rt=13.64 minutes; purity ≧90% (220 nm). MS (FAB$^+$): 1166.35 (MH$^+$).

NTA-βAla-βAla-NH—(CH$_2$)3—NHCO—AO (Compound No. 20)

Glycerine tert.butyl ester Hcl (3.34 g, 20 mmol) was dissolved in aqueous sodium carbonate. The free tert.butyl ester was extracted into dichloro methane (3×100 ml) and dried above sodium carbonate. The solvent was removed in vacuo giving 2.44 g (92%) of the free tert.butyl ester. DIEA (20 ml) was added followed by benzyl-2-bromoacetate (8 ml). The mixture was heated to reflux for 45 min, then cooled to room temperature, diluted with ethyl acetate and washed with aqueous sodium carbonate followed by water. The solvent was removed in vacuo and the NTA-tert-butyl-dibenzyl ester purified on a silicagel column using a gradient of 10–30% ethyl acetate in hexane as eluent. Yield 7.1 g (83%). The tert.butyl ester was cleaved by refluxing for two hours with a 1:1 mixture of TFA and dichloro methane giving NTA-dibenzyl ester as the trifluoro acetate.

Compound no. 9 (0.394 g, 0.809 mmol), NTA-dibenzyl ester (0.383 g, 1.03 mmol) and BOP (0.456 g, 1.03 mmol) was suspended in DMF (20 ml). DIEA (0.87 ml, 5 mmol) was added, and the mixture was left overnight. Water was added (20 ml), and the precipitated product was collected by filtration and washed several times with water. The crude product was dissolved in hot ethanol (75 ml), and the solution was decolorised with activated carbon. Water was added (50 ml), and the solution was concentrated to approx. 60 ml. The mixture was left overnight at room temperature, and the precipitated product was filtered off. The solid was suspended in THF (10 ml) and 0.5 M LiOH (5 ml) was added. The solution was stirred at room temperature for 2.5 hour, then THF was removed in vacuo and 10% phosphoric acid added. The product was collected by filtration, washed with water and dried in vacuo. Yield: 0.214 g (42% from compound no. 9); Mp: 158–163° C.; TLC (methanol/pyridine/acetic acid 80:20:6): $R_f$=0.42.

MS (FAB$^+$): 624.23 (MH$^+$); 646.20 (M+Na$^+$).

Anthraquinone-2-carboxylic acid chloride (Compound No. 21)

Anthraquinone-2-carboxylic acid (2.52 g, 10 mmol) was suspended in dichloro methane (100 ml). Thionyl chloride (50 ml) was added and the mixture heated to reflux in a nitrogen atmosphere for several hours giving a clear yellow solution. Dichloro methane and excess thionyl chloride was removed in vacuo giving a yellow solid. The solid was filtered off, washed several times with petroleum ether and dried in vacuo. Yield 2.69 g (99% from anthraquinone-2-carboxylic acid); MP: 143–144.5° C.; TLC (analyzed as the methyl ester: a small sample of the acid chloride was dissolved in dry methanol and analyzed immediately using ethyl acetate as eluent); $R_f$=0.68. MS (FAB$^+$): 307.1 (MH$^+$).

AO—CO-PEG2000 (Compound No. 22)

PEG2000 (2.00 g, 1 mmol) was dissolved in toluene (100 ml). 50 ml of the toluene was distilled off and the solution cooled to r.t.. Anthraquinone-2-carboxylic acid chloride (0.271 g, 1 mmol) followed by pyridine (1.6 ml, 20 mmol) was added and the mixture heated to reflux in a nitrogen atmosphere for one hour. Toluene and excess pyridine was removed by distillation, then water (100 ml) was added and residual toluene removed by azeotrope distillation. The target compound was isolated by freeze drying from water. Yield 2.28 g (102%). HPLC (Delta Pak 5$\mu$ $C_{18}$ 3.9×150 mm; buffer A: 0.1% TFA in water; buffer B: 0.1% TFA in acetonitrile/water 9:1; gradient: 25% A+75% B for 2 minutes, then a linear gradient from 25%+75% B to 100% B over 10 minutes, then 100% B for 10 minutes; $R_t$=2.4 min (anthraquinone-2-carboxylic acid: 2.6% (330 nm)); $R_t$=3.69 min (AQ—CO-PEG2000: 78.9% (330 nm)); $R_t$=7.08 min (AQ—CO-PEG2000-CO—AQ: 18.5% (330 nm)).

Example 2

Figure 1:
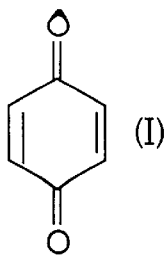
FIG. 1 shows illustrations of applicable basic quinone compounds (I)–(XXXVI) according to the invention.
Figure 1:
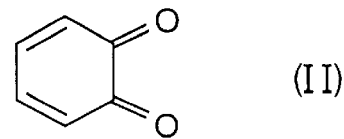
Figure 1:
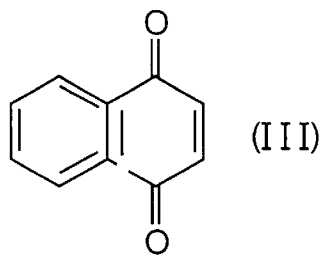
Figure 1:
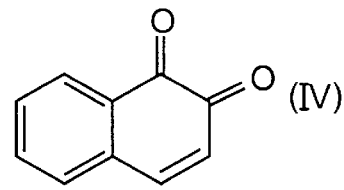
Figure 1:
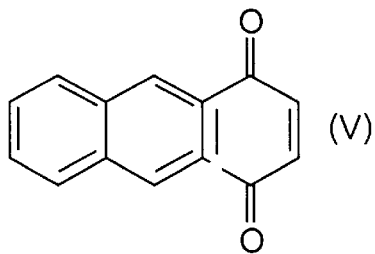
Figure 1:
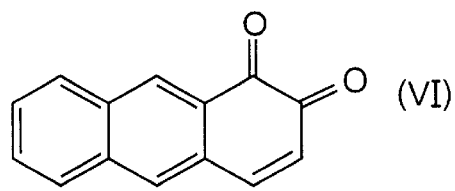
Figure 1:
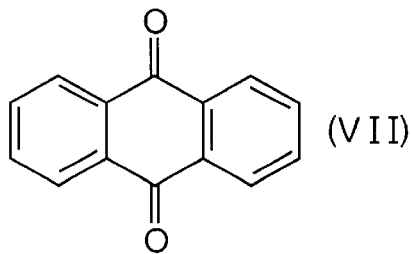
Figure 1:
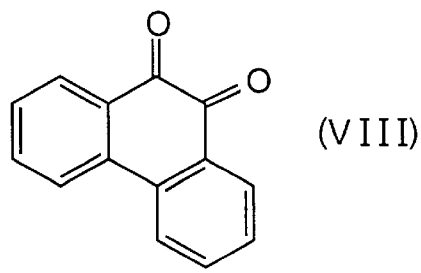
Figure 1:
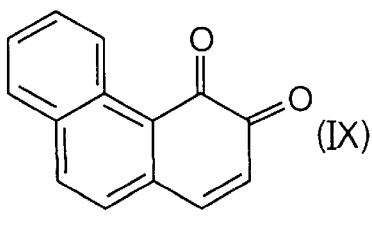
Figure 1:
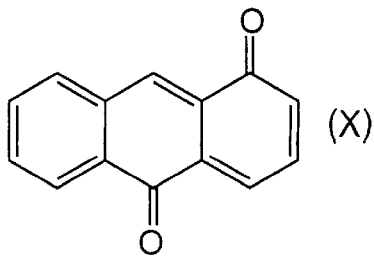
Figure 1:
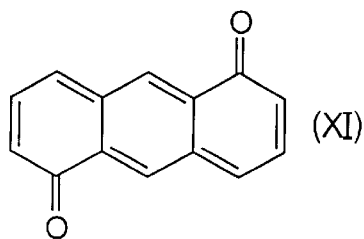
Figure 1:
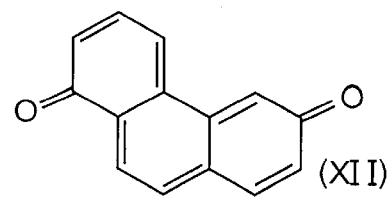
Figure 1:
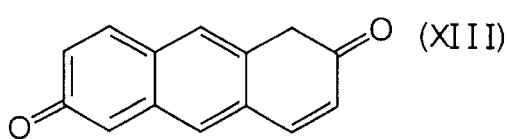
Figure 1:
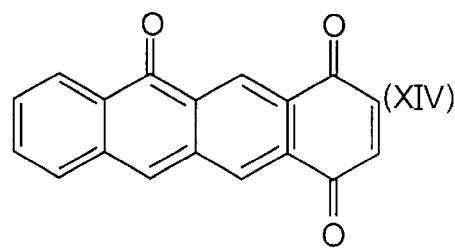
Figure 1:
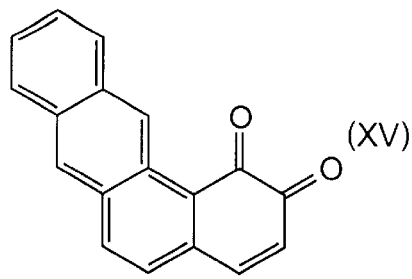
Figure 1:
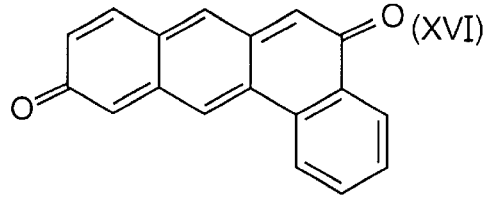
Figure 1:
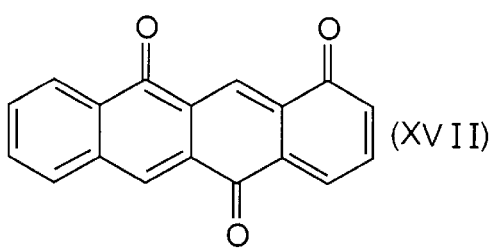
Figure 1:
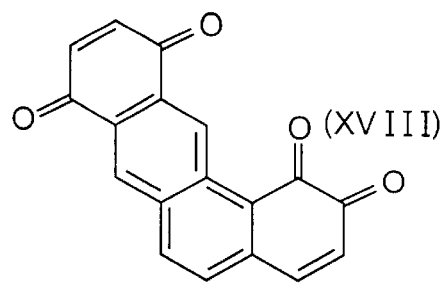
Figure 1:
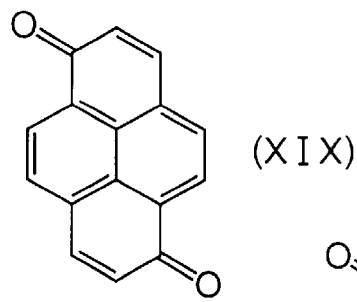
Figure 1:
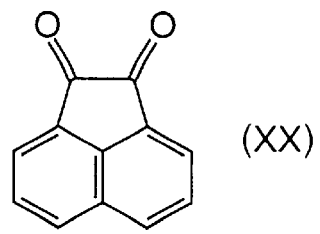
Figure 1:
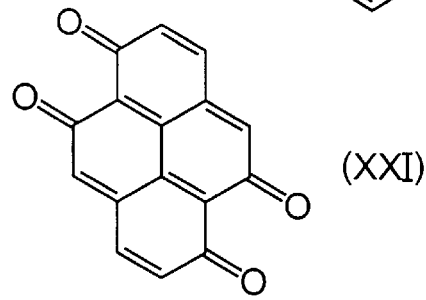
Figure 1:
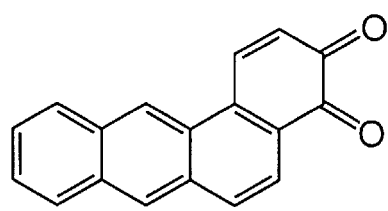
Figure 1:
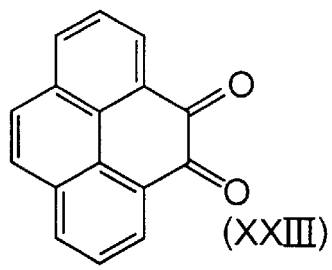
Figure 1:
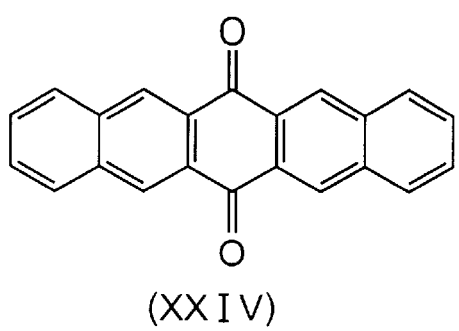
Figure 1:
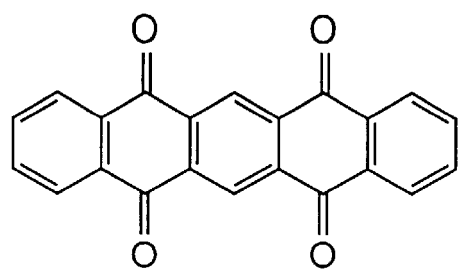
Figure 1:
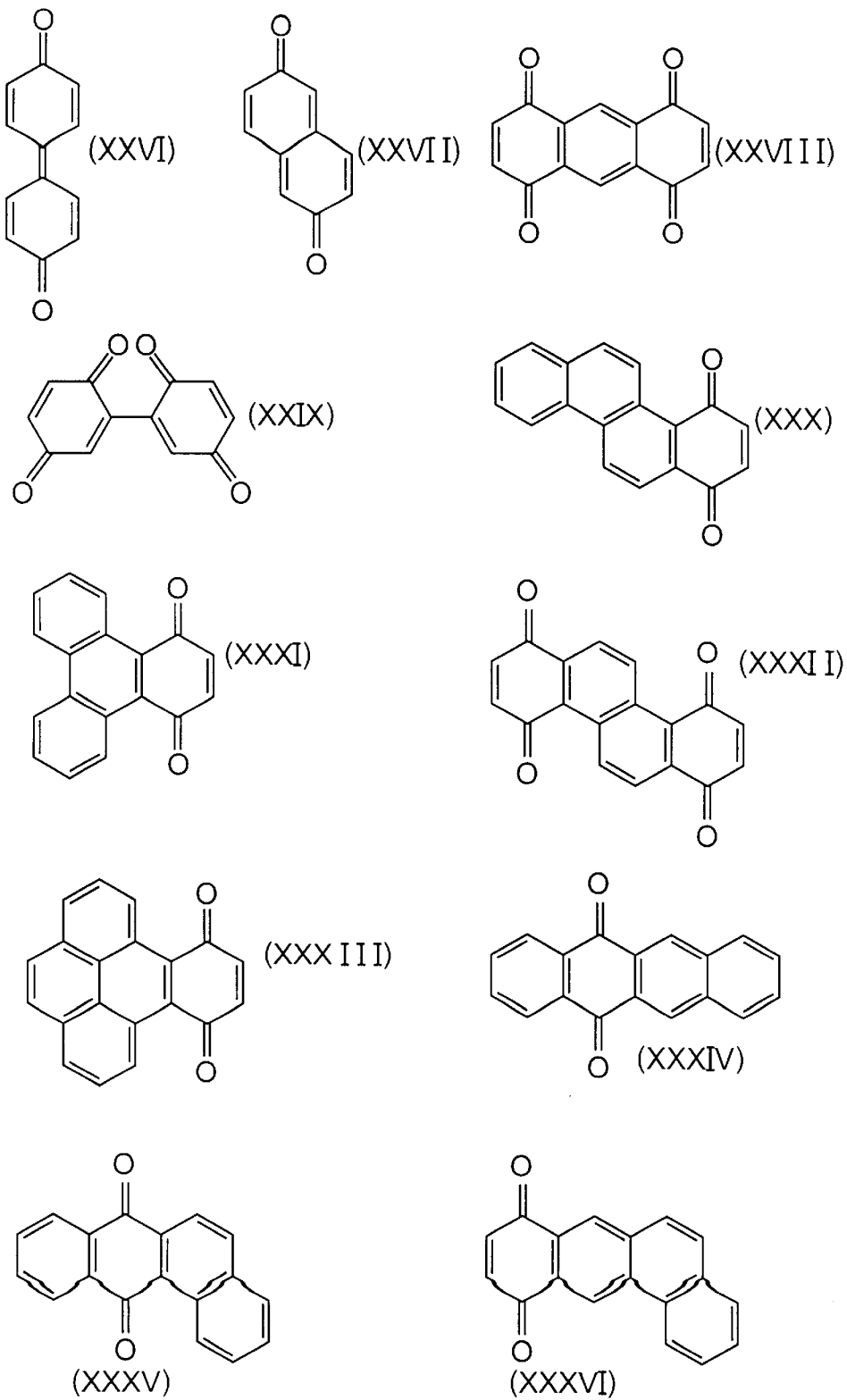
Figure 2:
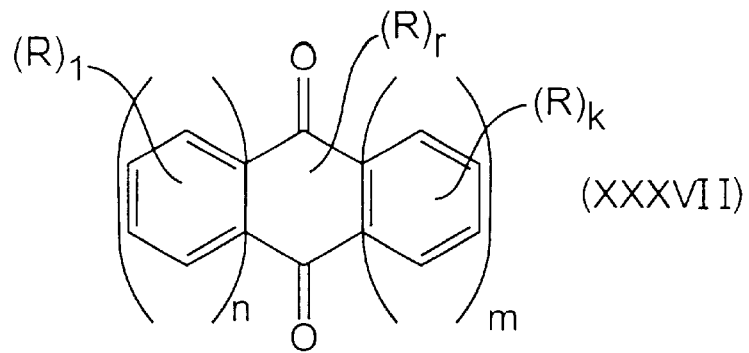
FIG. 2 shows particularly preferred quinones (XXXVII)–(XXXIX) according to the invention.
Figure 2:
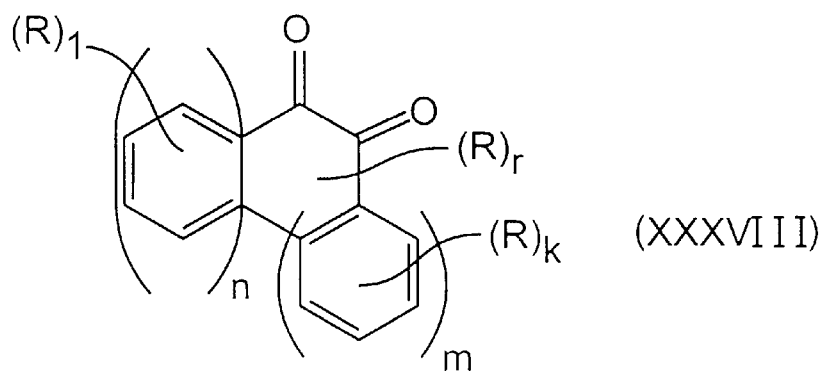
Figure 2:
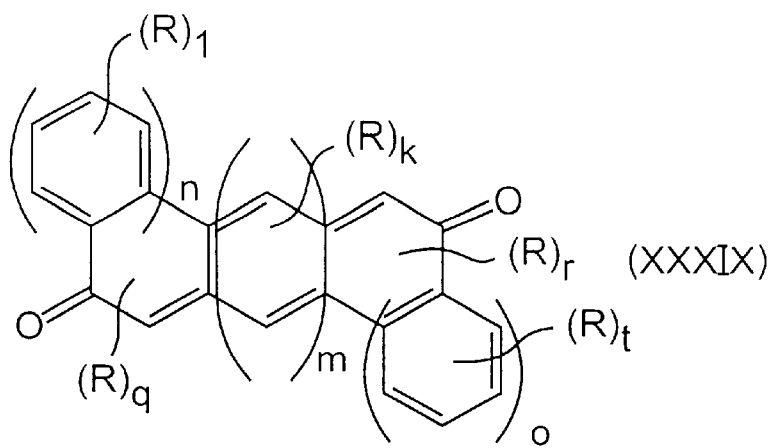
Figure 3:
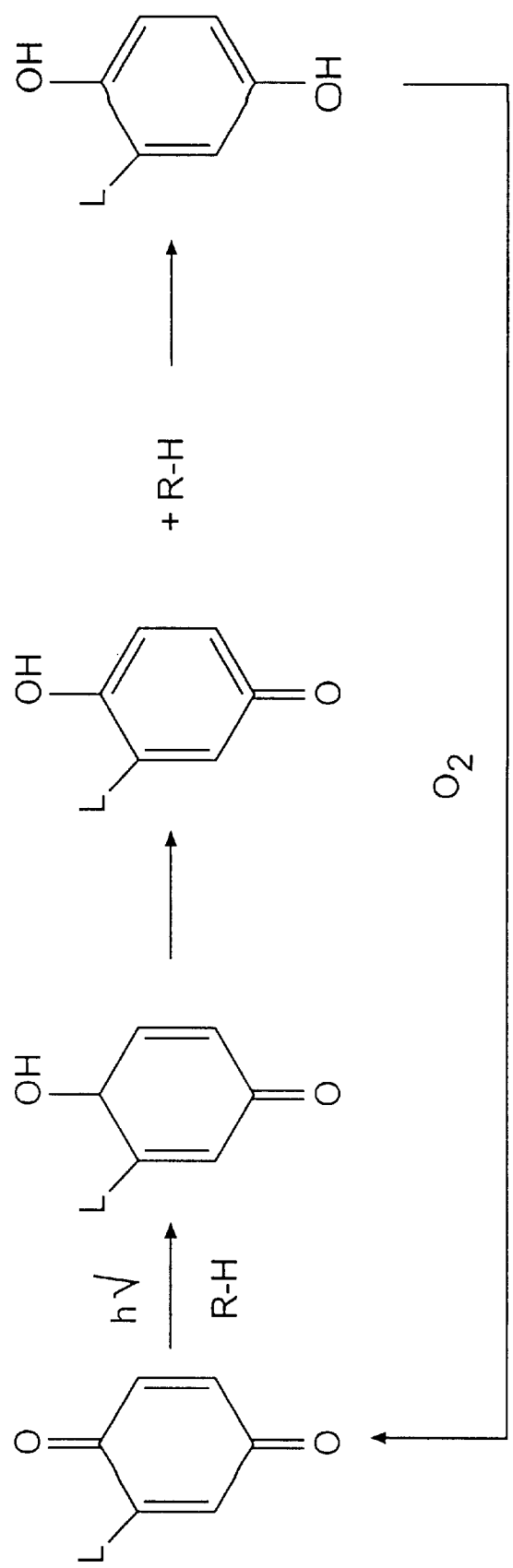
FIG. 3 shows an illustration of recycling of reduced quinones.

Compound no. 5 in Example 1 substituted antraquinone (VII) (in this experiment designated Q1) and compound no. 3 in Example 1 substituted phenanthrenequinone (VIII) (in this experiment designated Q2) and a selected number of other photoprobes were studied for absorbance in the wavelength range from 190–820 nanometers. Compound XXVI correspond to the structure shown in FIG. 1.

The following absorption maxima and extinction coefficient ($\epsilon$) was found (see Table 1).

TABLE 1

UV/data of photoprobes (n.a. = no absorption)

| Compound | $\lambda_{max}$ (nm) | $\epsilon_{max}$ (M$^{-1}$ cm$^{-1}$) | $\lambda_{max}$ (nm) | $\epsilon_{max}$ (M$^{-1}$ cm$^{-1}$) | $\lambda_{max}$ (nm) | $\epsilon_{max}$ (M$^{-1}$ cm$^{-1}$) |
|---|---|---|---|---|---|---|
| Azidobenzene | 247 | 7900 | 315 | 80 | (n.a.) | — |
| Benzophenone | 260 | 14000 | 333 | 110 | (n.a.) | — |
| Anthracenequinone | 252 | 39000 | 325 | 4700 | 390 | 110 |
| Phenanthrenequinone | 266 | 29000 | 328 | 4300 | 425 | 1400 |
| Q1 | 256 | 49000 | 332 | 4700 | 390 | 310 |
| Q2 | 266 | 39000 | 330 | 5700 | 424 | 1400 |
| XXVI | 253 | 2500 | 263 | 2350 | 398 | 69000 |

Example 3

Introduction of Primary Amino Groups onto Polystyrene Surfaces by UV Grafting

Figure 8A:
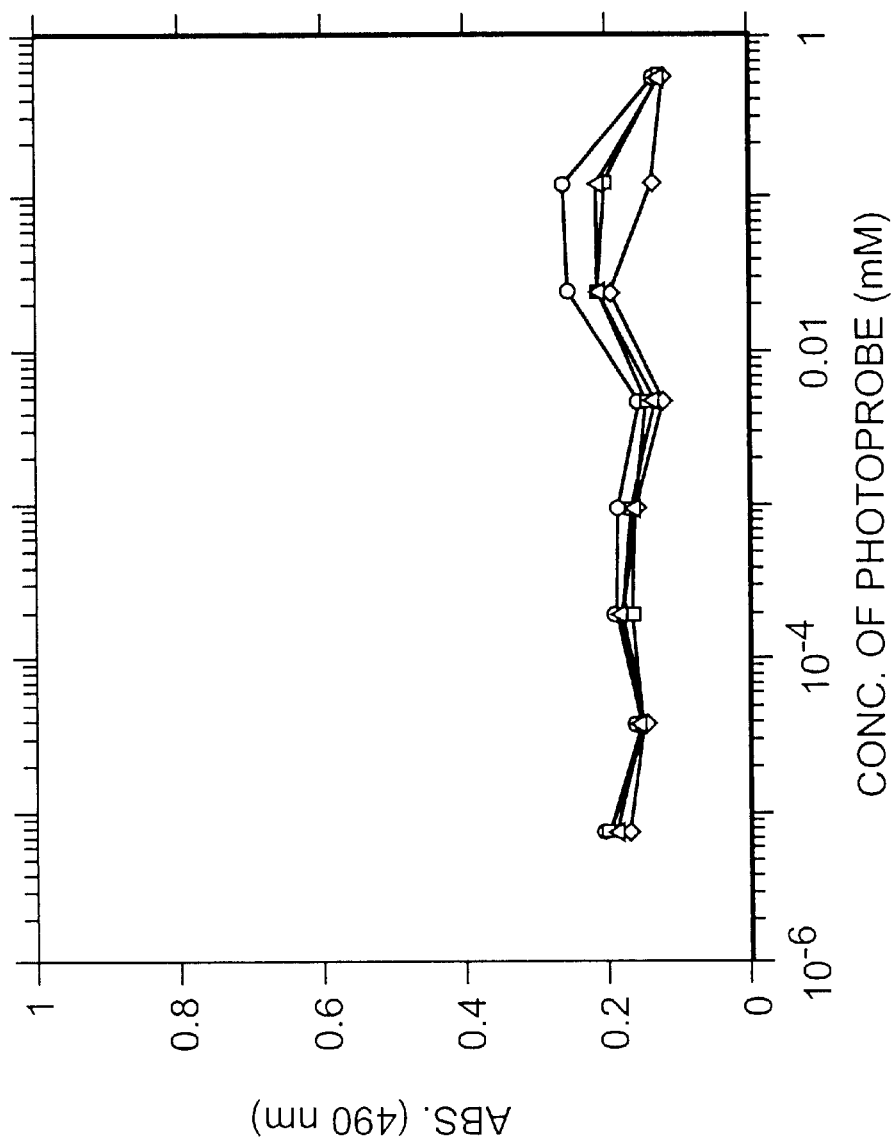
FIG. 8a shows a UV grafting of phenanthrene quinone amine compound no. 3 onto polystyrene surfaces (PolySorp®). Effect of photoprobe concentration and irradiation time. ◇ No UV irradiation (control); □ 5 min. irradiation; ▲ 7 min.; ○ 10 min.
Figure 8B:
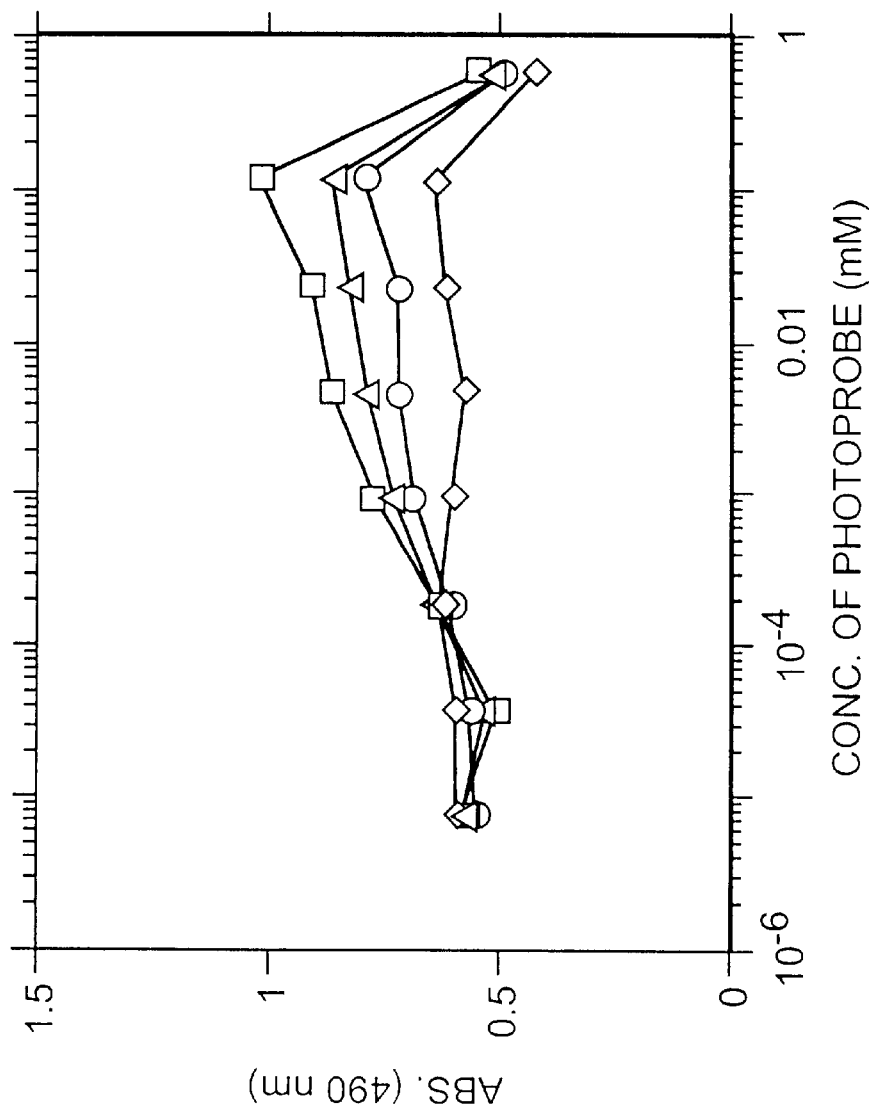
FIG. 8B shows a grafting of phenanthrene quinone amine compound no. 3 onto polystyrene surfaces (Nunclon® Delta treated). Effect of photoprobe concentration and irradiation time. ◇ No. UV irradiation (control); □ 5 min. irradiation; ▲ 7 min.; ○ 10 min.
Figure 9A:
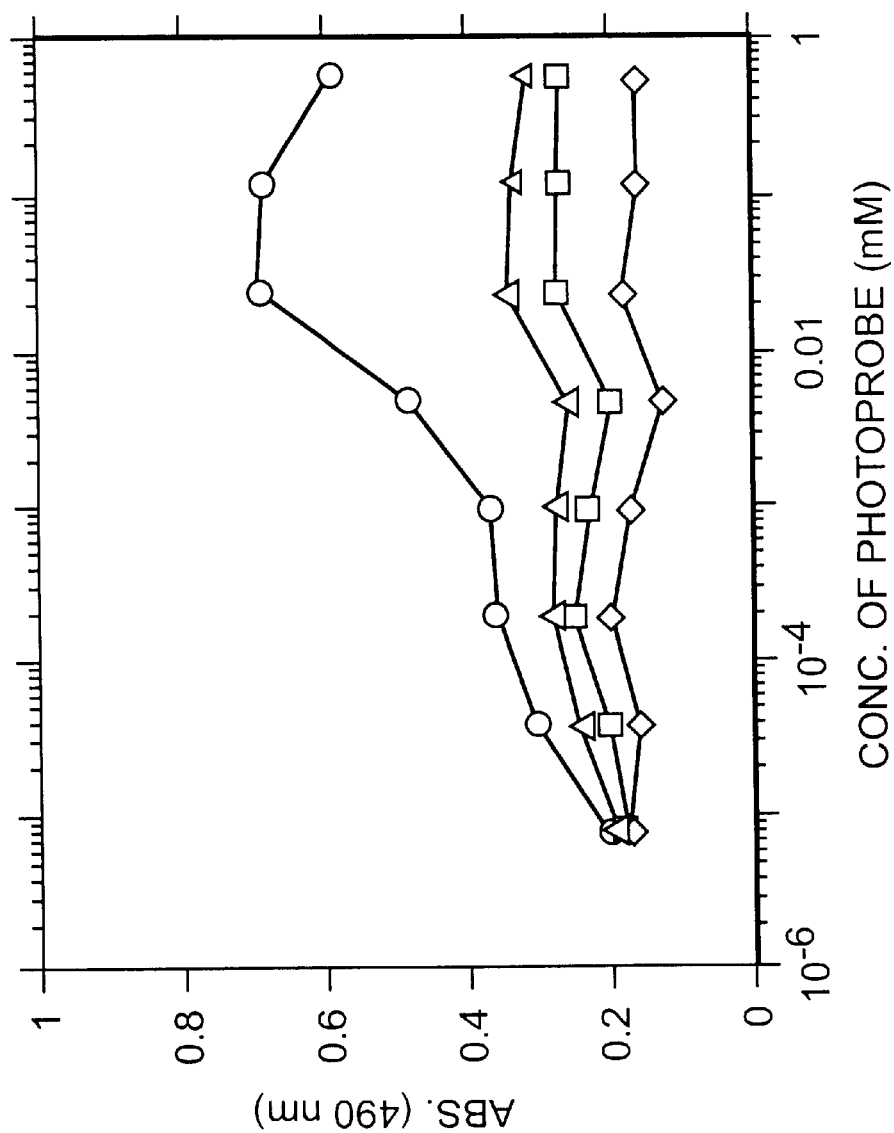
FIG. 9a shows a grafting of anthraquinone amine compound no. 5 onto polystyrene surfaces (PolySorp®). Effect of photoprobe concentration and irradiation time. ◇ No. UV irradiation (control); □ 5 min. irradiation; ▲ 7 min.; ○ 10 min.
Figure 9B:
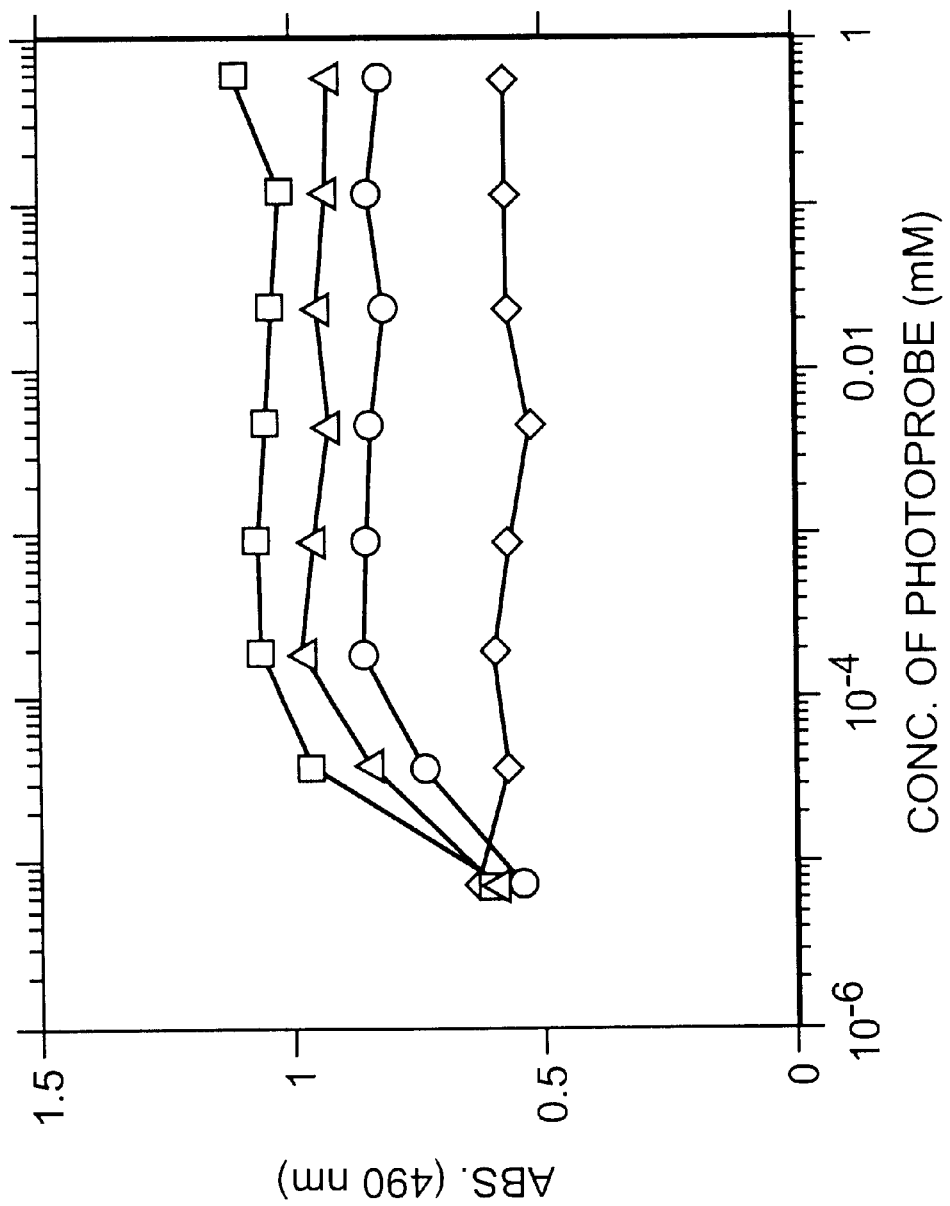
FIG. 9b shows a UV grafting of anthraquinone amine compound no. 5 onto polystyrene surfaces (Nunclon® Delta treated). Effect of photoprobe concentration and irradiation time. ◇ No. UV irradiation (control); □ 5 min. irradiation; ▲ 7 min.; ○ 10 min.

The effect of quinone type as well as the effect of photoprobe concentration and irradiation time on the introduction of primary amino groups were tested with phenanthrene quinone amine compound no. 3 and anthraquinone amine compound no. 5 on two types of polystyrene: 1) Nunc-Immuno® Module F16 PolySorp (untreated polystyrene, Nunc cat. no. 467679); 2) non-sterile Nunc F96 Nunclon® Delta treated plates). The quinone amines compound no. 3 and compound no. 5 were dissolved in distilled water, and 100 $\mu$l was added to each well of the ELISA plates in a five-fold dilution series with a start concentration of 0.58 $\mu$M of the photoprobes. The plates were placed 14 cm under the UV lamp (Philips HPA 400: the lamp emits low energy UV-A and UV-B light mainly between 300 and 400 nm), and they were irradiated for 5, 7 and 10 minutes, respectively. The wells were rinsed three times with demineralized water and dried for 50 minutes at 60° C. Plates containing the photoprobes were kept in the dark during photolysis as controls. Biotin-succinimide ester (Sigma cat. no. H 1759) in PBS buffer (phosphate buffered saline: 0.15 M Na$^+$, 4.2 mM K$^+$, 7.9 mM phosphate, pH 7.2) was added (100 $\mu$l/well), and the wells were allowed to incubate overnight at room temperature. The wells were washed three times with CovaBuffer (PBS buffer pH 7.2+2 M NaCl+4.1 mM MgSO$_4$+0.5% (v/v) Tween 20$^R$) leaving CovaBuffer (PBS buffer pH 7.2+2 M NaCl+4.1 mM MgSO$_4$+0.5% (v/v) Tween 20$^R$) leaving CovaBuffer in the wells for 10 minutes after the last wash. The wells were aspirated and avidin mix (4 $\mu$g/ml avidin (Sigma cat. no. A 9390) and 0.13 $\mu$g/ml Horse Radish Peroxidase conjugated avidin (DAKO cat. no. P 347) in PBS buffer pH 7.2) was added to each well (100 $\mu$l/well). The wells were incubated for 2 hours at room temperature and washed twice with CovaBuffer as described above. The amount of bound protein was quantified by measuring the peroxidase activity in citrate buffer (0.1 M, pH 5.0) containing 0.015% (v/v) H$_2$O$_2$ and 0.6 mg/ml OPD (Sigma cat. no. P 8412) as chromogenic substrate. The enzymatic reaction was terminated after 6 minutes by addition of H$_2$SO$_4$ (2M, 100 $\mu$l/well), and the color reaction quantified by measuring the absorption at 490 nm on the ELISA reader (InterMed Immuno reader NJ 2000). The results for phenanthrene quinone amine compound no. 3 are shown in FIGS. 8a and 8b. On PolySorp® surfaces (FIG. 8a) no significant higher signal was observed than the control level, while on Nunclon® Delta treated surfaces higher signals were observed for all irradiation times with a maximum with 0.116 mM photoprobe concentration and 5 minutes irradiation time. Results for anthraquinone amine compound no. 5 are shown in FIGS. 9a and 9b. On PolySorp® surfaces (FIG. 9a) a significant higher signal than the background (control) was clearly seen. Maximum was obtained with a photoprobe concentration between 0.116 mM and 0.0232 mM and 10 minutes irradiation time. On Nunclon® Delta treated surfaces significant higher signals than the background (control) were observed at all irradiation times with concentrations of the photoprobe higher than 3.72·10$^{-5}$ mM.

The effect of varying spacer arms was tested on anthraquinone amines compounds nos. 5, 7 and 9. The anthraquinone amines were dissolved in distilled water to a concentration of 0.1 mM photoprobe, and 100 $\mu$l was added to each well of a Nunc-Immuno® Module F16 PolySorp 35 and a non-sterile Nunc F96 (Nunclon® Delta treated) plate.

Figure 10:
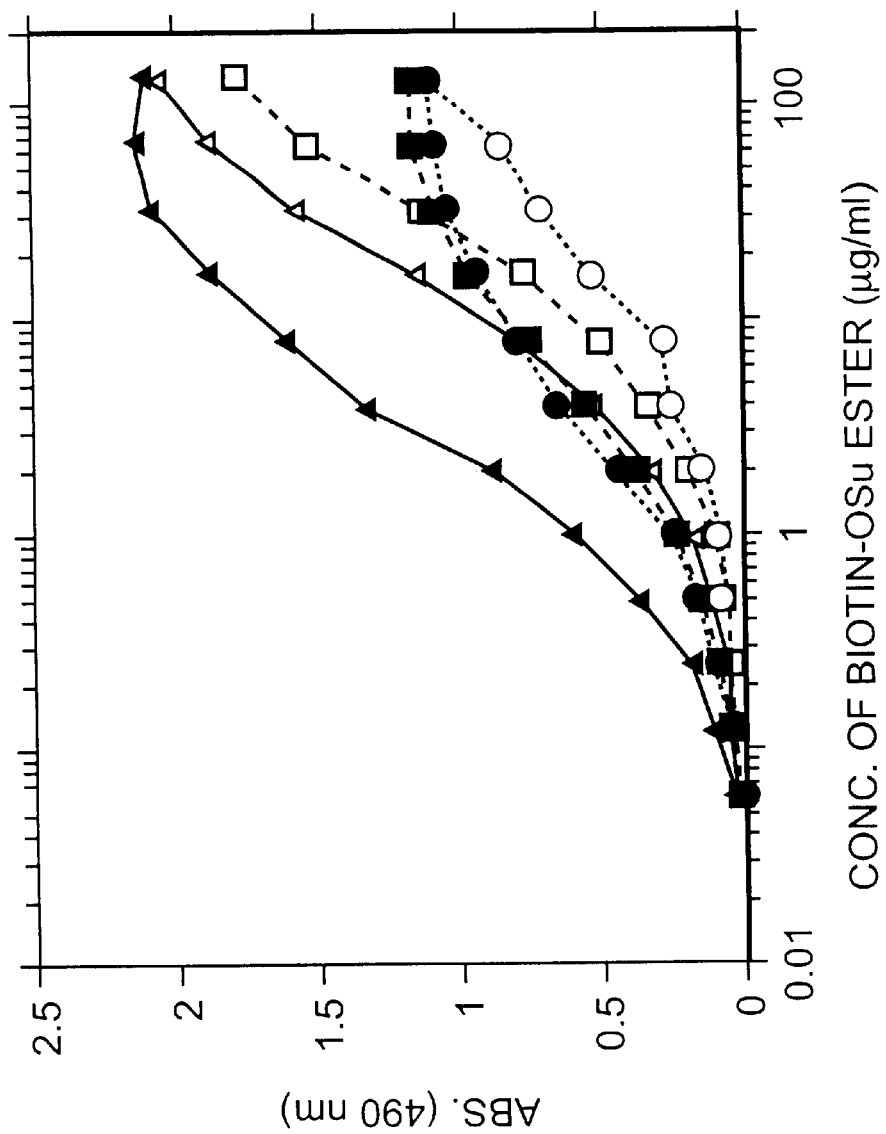
FIG. 10 shows a UV grafting of anthraquinone amines compounds nos. 5, 7 and 9 onto polystyrene surfaces. Effect of spacer arm length on signal strength. Open symbols: results on Nunclon® Delta treated surfaces; closed symbols: results on PolySorp plates. ○/● Amine 5, □/■ Amine 7; △/▲ Amine 9.

The plates were placed 10 cm below the UV lamp and irradiated for 10 minutes. The wells were rinsed three times with demineralized water and dried for 50 minutes at 60° C.. A two-fold dilution series of biotin-succinimide ester in PBS buffer was added (100 μl/well), and the wells were allowed to incubate overnight at room temperature. The wells were washed three times with CovaBuffer, avidin mix was added, and the amount of bound protein quantified as described earlier. The results are shown in FIG. 10 and clearly indicate the effect of the linker length. Compound no. 9, with two β-alanine units, showed the overall highest signal when grafted on PolySorp®. Lower signals were seen, when compound no. 9 was grafted on Nunclon® Delta treated plates. However, the signal was still higher than for compound no. 5 and compound no. 7, indicating the advantage of having an optimal spacer length between the photoprobe and the primary amino group.

The uniformity of photochemically grafted amino groups on polystyrene surfaces was tested with anthraquinone amine compound no. 9. Compound no. 5 was dissolved in distilled water to a concentration of 0.1 mM photoprobe. 100 μl of the solution was added to each well in four non-sterile Nunc F95 (Nunclon® Delta treated) plates, placed 10 cm below the UV lamp and irradiated for 10 minutes. Each well was washed three times with demineralized water and dried for 50 minutes at 60° C. Biotin-succinimide ester in PBS buffer was added (125 μg/ml, 100 μl/well), and the wells allowed to incubate overnight at room temperature. After washing three times with CovaBuffer avidin mix was added to each well, and the amount of bound protein was quantified as described earlier. The results are shown in Table 2.

TABLE 2

Uniformity of primary amino groups polystyrene surfaces by UV grafting. Mean of four plates.

| Mean (Abs. 490 nm) | St. dev. | % CV |
| --- | --- | --- |
| 1.959 | 0.063 | 3.2 |

Figure 11:
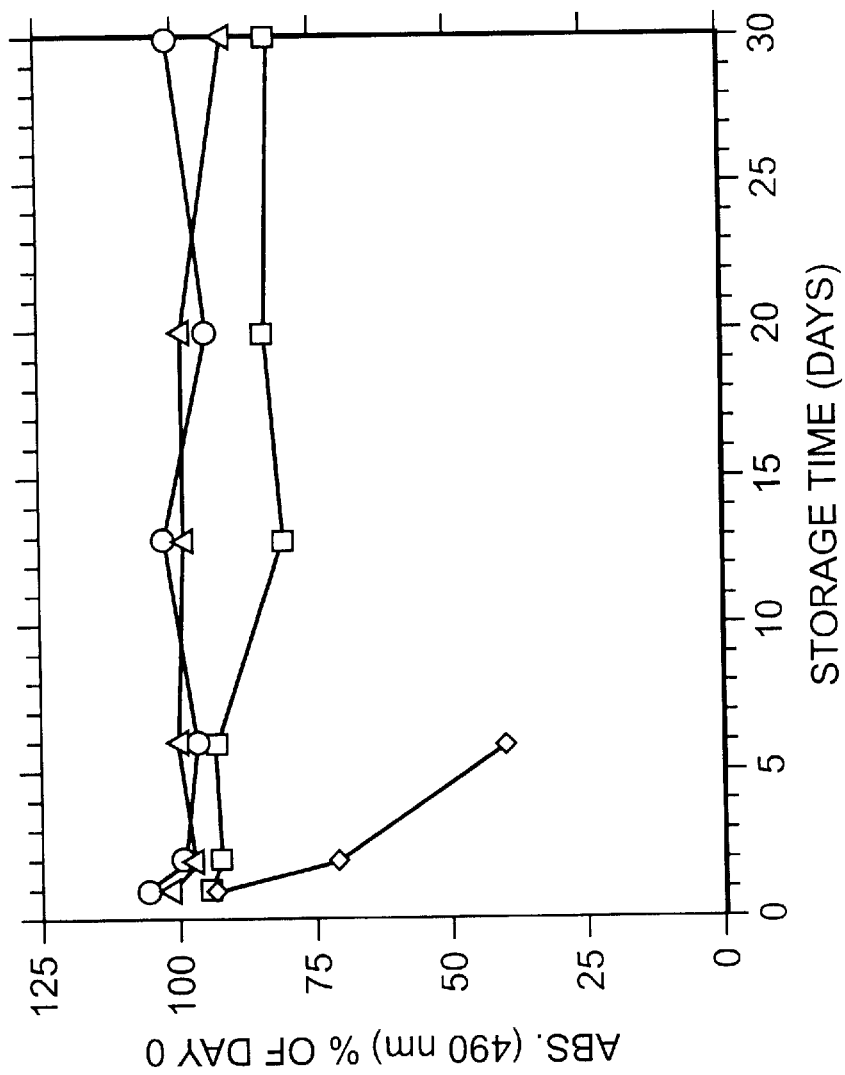
FIG. 11 shows the storage stability of anthraquinone amine compound no. 9 UV grafted onto Nunclon® Delta treated polystyrene surfaces. Values are given relative to day zero. ○ Storage temperature 4° C.; ▲ 20° C.; □ 37° C.; ◇ 60° C.
Figure 12:
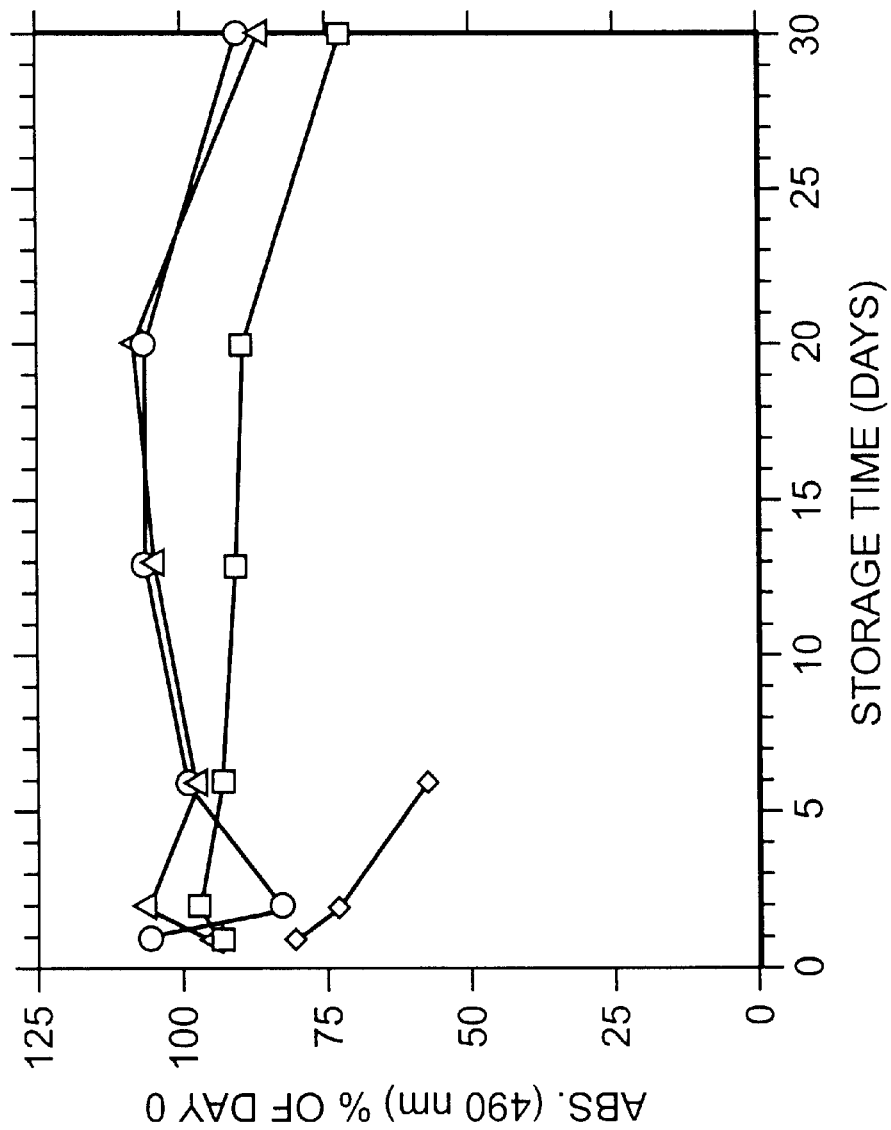
FIG. 12 shows the storage stability of anthraquinone amine compound no. 9 UV grafted onto PolySorp® polystyrene surfaces. Values are given relative to day zero. ○ Storage temperature 4° C.; ▲ 20° C.; □ 37° C.; ◇ 60° C.

The storage stability of photochemically grafted amino groups on polystyrene surfaces was tested with anthraquinone amine compound no. 9. Compound no. 5 was dissolved in distilled water to a concentration of 0.1 mM photoprobe. 100 μl of the solution was added to each well in non-sterile Nunc F96 (Nunclon® Delta treated) plates and Nunc-Immuno® Module F8 PolySorp plates (Nunc. cat. no. 469078), placed 10 cm below the UV lamp and irradiated for 10 minutes. Each well was washed three times with demineralized water and dried for 50 minutes at 60° C. One plate of each type was packed in sealed plastic bags and stored for up to 30 days at 4° C., 20° C., 37° C., and 60° C. Plates were taken out for testing at intervals of 1, 2, 6, 13, 20, and 30 days of storage. One plate of each type was used for stability testing. The plates were incubated with biotin-succinimide ester followed by avidin mix, and the amount of bound protein was quantified as described earlier. Results are shown in FIGS. 11 and 12. All date have been normalized relative to day zero (no storage). The results show that no significant reduction in activity is seen at a store temperature of 37° C. or below, while plates stored at 60° C. showed a slight decrease in signal.

Introduction of Carboxylic Acids onto Polystyrene Surfaces by UV Grafting

Figure 13:
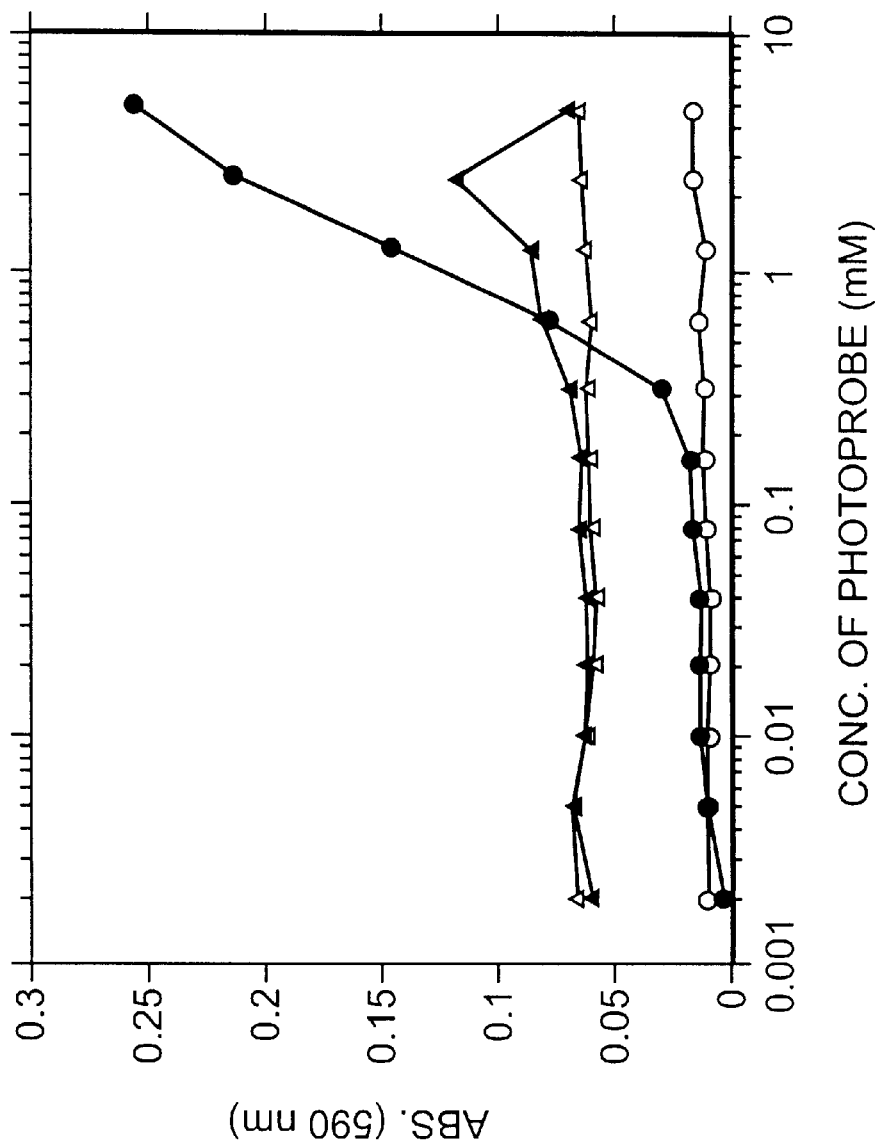
FIG. 13 shows the UV grafting of anthraquinone carboxylic acid derivative compound no. 13 onto polystyrene surfaces. Open symbols: results with no UV irradiation (control); closed symbols: results after 10 min. UV irradiation. ○/● PolySorp® plates; △/▲ Nunclon® Delta treated plates.

The anthraquinone carboxlylic acid derivative compound no. 13 was dissolved in 0.1 M LiOH and diluted with distilled water to a concentration of 5 mM. A two-fold dilution series of the photoprobe (100 μl/well) was made in non-sterile Nunc F96 (Nunclon® Delta treated) plates and in Nunc-ImmunoR Module F8 PolySorp plates. The plates were placed on a shaker for one hour at 50° C. before UV irradiation. the wells were aspirated and placed 14 cm from the UV lamp and irradiated for 10 minutes. Non-irradiated plates were used as control. The wells were rinsed three times with demineralized water and crytal violet (Merck cat. no. 1408, 15 mg in 100 ml of distilled water) added to each well (100 μl/well). The plates were incubated for 30 minutes at room temperature, washed three times with demineralized water and dried for 30 minutes at 60° C. Dissolution of bound crystal violet was done by adding a solution of 1 M HCl in 96% ethanol to each well. The results were read on an InterMed Immuno reader NJ 2000 at 590 nm and are shown in FIG. 13. As crystal violet binds as an ion pair to carboxylic acids, an increase in signal will indicate the presence of immobilized carboxylic acid groups on the surface. No signal was obtained on plates that had not been UV irradiated, while a significant increasing signal with increasing concentration of the photoprobe was seen on PolySorp® surfaces.

Example 4

Covalent Coupling of a Peptide onto Polystyrene Surfaces by UV Grafting

Peptide compound no. 19, N-terminally anthraquinone substituted, was dissolved in distilled water (0.1 mg/ml).

Figure 14:
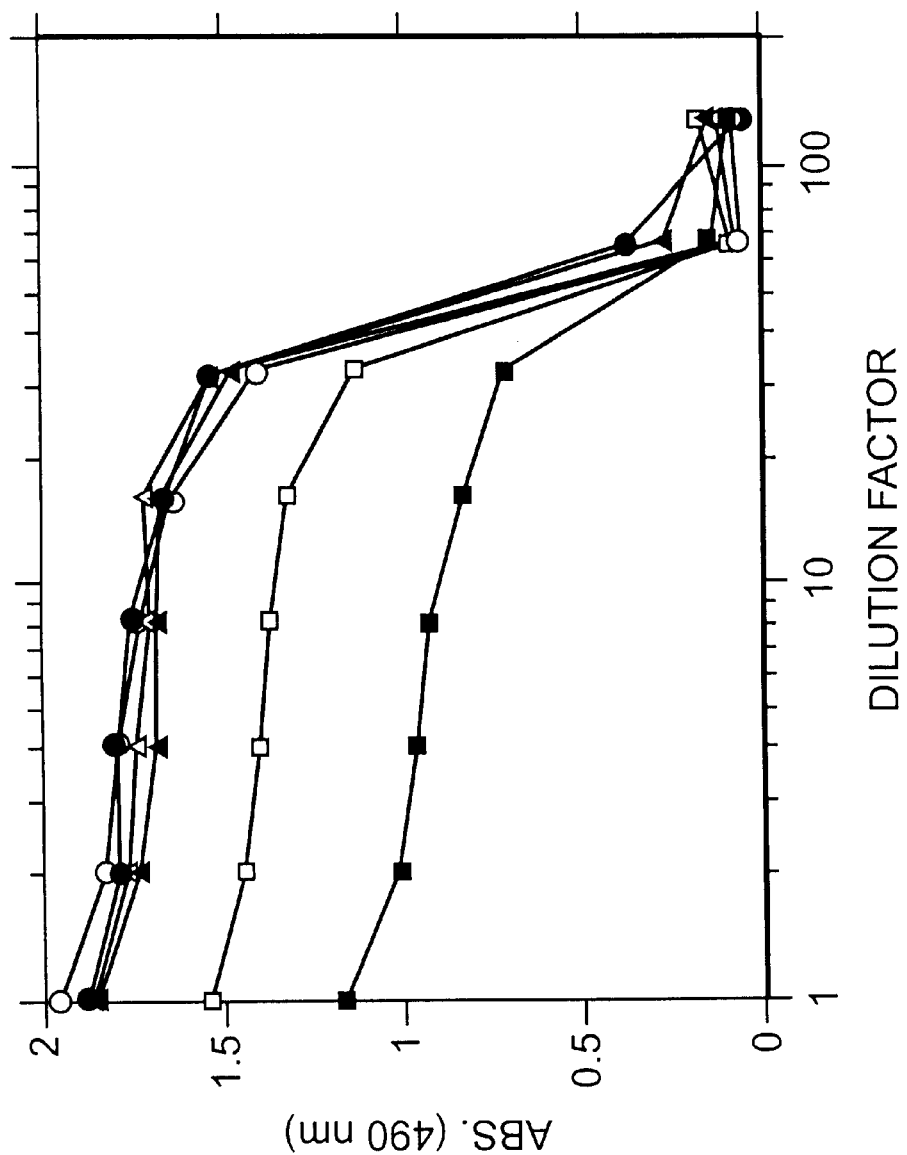
FIG. 14 shows a UV grafting of peptide compound no. 19, N-terminally anthraquinone substituted, onto polystyrene surfaces: Effect of irradiation time and concentration of Hyb 161-2 anti peptide monoclonal antibody. 2 min. irradiation; ● 5 min.; ▲ 10 min.; ▲ 15 min.; □ 30 min.; ■ 60 min.

100 μl was added to each well of two Nunc-Immuno® Module F16 PolySorp®—except for row A—which was used as blank control. One strip (2×8 wells) at a time was irradiated 2, 5, 10, 15, 30, and 60 minutes, respectively (14 cm under the UV lamp). After UV irradiation the plates were rinsed three times with 0.4 M NaOH containing 0.25% Tween $20^R$, and three times with PBS buffer. Immobilized peptide was detected with a monoclonal anti-peptide antibody (culture supernatant Hyb 161-2 from Statens Seruminstitut, Copenhagen, Denmark). A two-fold dilution series of the antibody in PBS-Tween® buffer was made in the Immuno Modules from row C and onwards (100 μl/well). In row A (peptide blank) undiluted culture supernatant was added, while row B was used as control without Hyb.161-2. The Immuno Modules were incubated for two hours at room temperature, and then washed three times with PBS buffer containing 0.05% Triton X-$100^R$. A mixture of rabbit anti-mouse (2 μg/ml DAKO code Z 259) and horse radish peroxidase conjugated goat anti-mouse (1:500, DAKO code P 447) was added to each well (100 μl), incubated for one hour at room temperature and washed three times as described above. OPD substrate (100 μl) was added to each well, and the substrate reaction was stopped after four minutes with 2 M $H_2SO_4$ (100 μl/well). The results are shown in FIG. 14 and clearly show that 30 the optimum irradiation time was between 2 and 15 minutes. Optimal dilutaion factor of Hyb 161-2 culture supernatant was approx. 10 and was used in the subsequent experiments.

Figure 15:
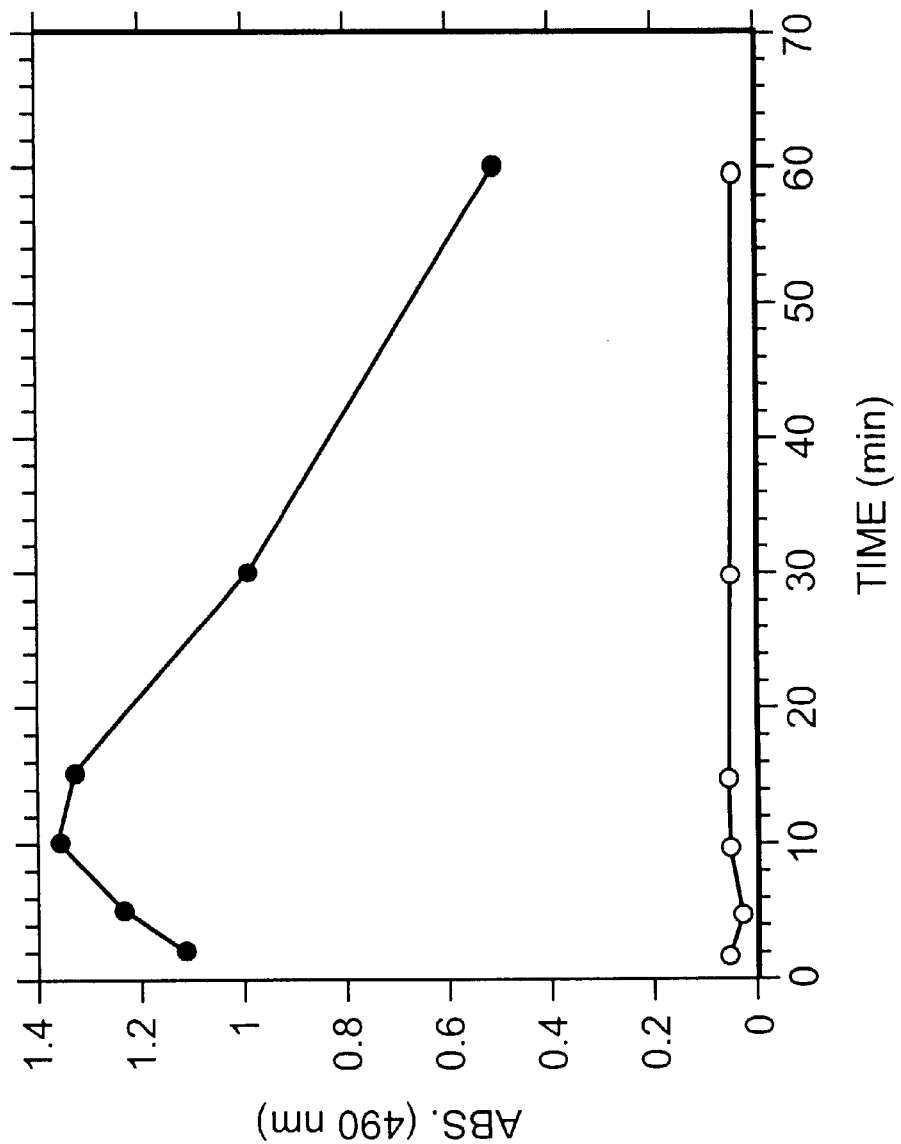
FIG. 15 shows a UV grafting of anthraquinone peptide compound no. 19 onto polystyrene surfaces. Effect of irradiation time with a constant concentration of Hyb 161-2 anti peptide monoclonal antibody. ○ Non specific binding with no Hyb 161-2 added; ● Hyb 161-2 added (1 mg/ml).

The effect of irradiation time was further investigated. the experiment was done as described above, except that a constant concentration of Hyb 161-2 (culture supernatant diluted 10 times) was used. The results are shown in FIG. 15 and clearly show that 10 minutes irradiation time was the optimum, but even after two minutes more than 80% of the maximum response was obtained. The background (non-specific reaction) in wells without peptide as well as wells without Hyb 161-2 was low. The decrease in signal at longer irradiation times is most likely due to increasing photo-chemical crosslinking of peptide backbone and the anthraquinone photoprobes leading to destruction of epitope recognition.

Figure 16:
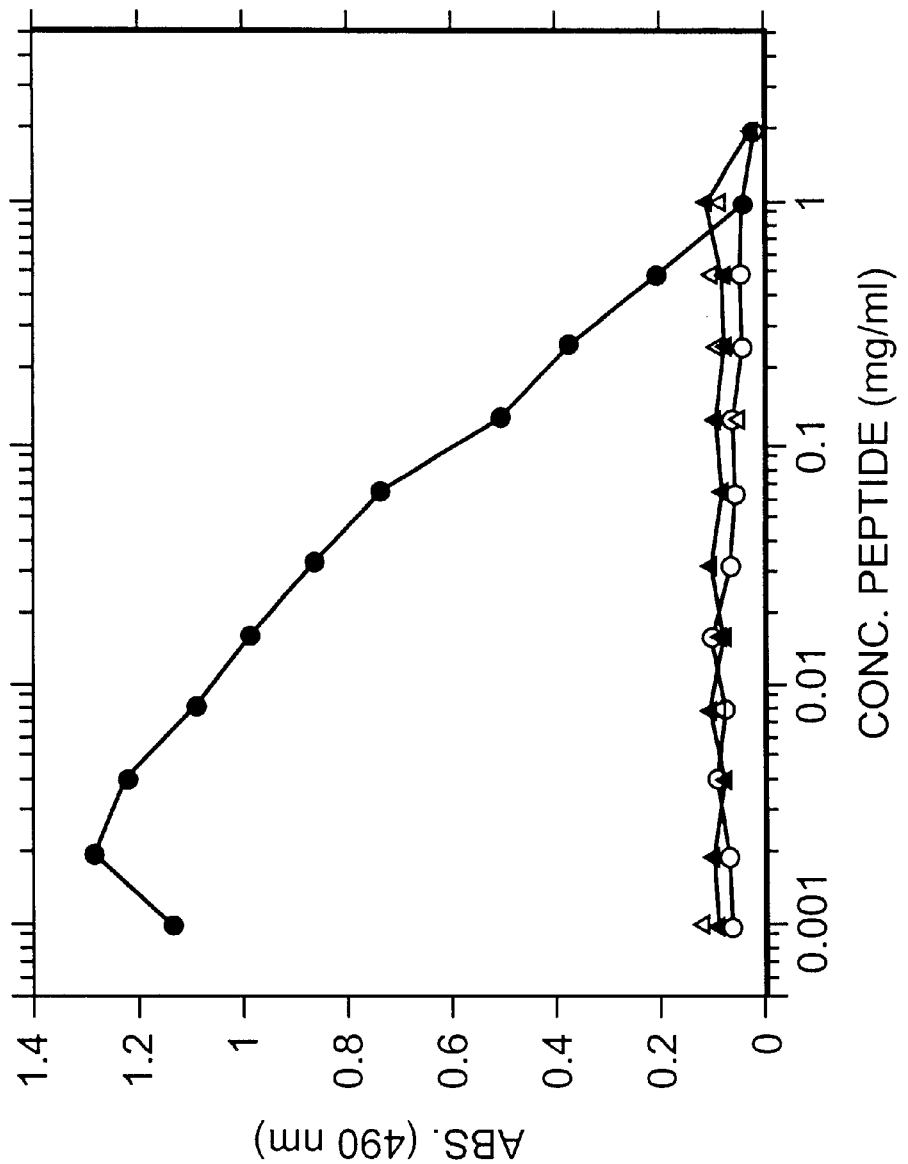
FIG. 16 shows a UV grafting of peptide compound no. 19, N-terminally anthraquinone substituted, onto polystyrene surfaces. Effect of peptide concentration. Closed symbols: 10 min. irradiation time; open symbols: no irradiation. ○/● Anthraquinone-peptide 9; △/▲ unsubstituted peptide.

The effect of peptide concentration was tested. The N-terminally anthraquinone substituted peptide compound no. 19 and peptide without the anthraquinone moiety (free N-terminus) were dissolved in water (2 mg/ml), and a two-fold dilution series made for each peptide solution in Nunc F16 PolySorb® Immuno Modules. The modules were irradiated for 10 minutes (14 cm under the UV lamp) and washed as described earlier. Immuno modules with anthraquinone-peptide and free peptide were kept in the dark during photolysis as controls. The amount of immobilized peptide was measured as described above, using a constant concentration of Hyb 161-2 (culture supernatant diluted 10 times). The results are shown in FIG. 16. Only irradiated wells containing the anthraquinone-peptide showed any detectable signal. Optimum concentration of the anthraquinone-peptide was approx. 4 μg/ml. The decrease in signal in higher concentrations can, as described earlier, be atributed to photochemical crosslinking of peptide backbone of the immobilized peptides, leading to destruction of epitope recognition. In addition to this, higher concentration of anthraquinone peptide in the solution, favours solution-phase photochemistry to the reaction with the polymer, leading to soluble photochemical crosslinked peptide aggregates, which is later removed in the washing steps.

Figure 17:
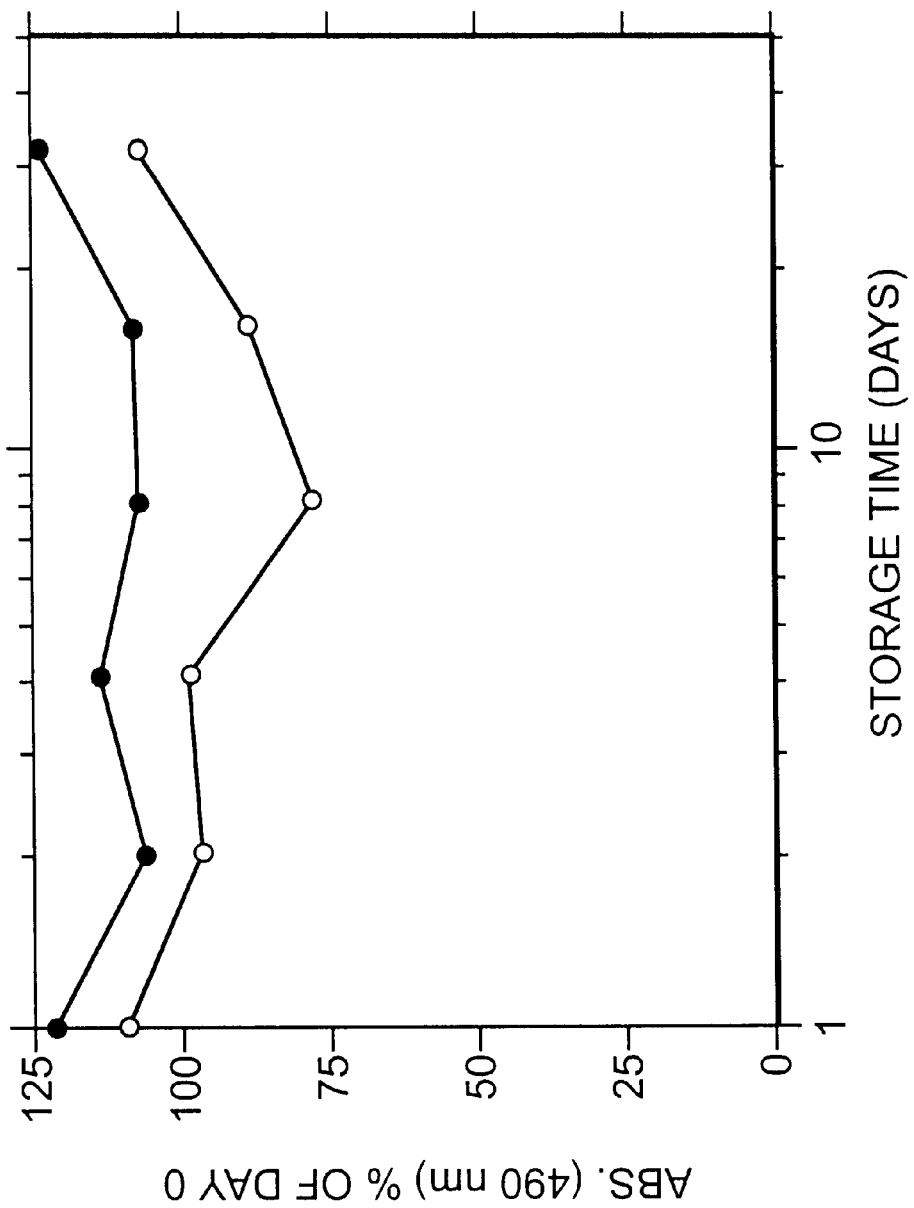
FIG. 17 shows the storage stability of UV grafted peptide compound no. 19. ○ Storage temperature 37° C.; ● 4° C.

The storage stability of the photochemically grafted peptide was investigated. The anthraquinone peptide number 19 was dissolved in distilled water (0.1 mM), and the solution was added to each well of a Nunc-Immuno® Module F16 PolySorp. The wells were irradiated for 10 minutes (14 cm under the UV lamp) and finally washed as described earlier. the wells were coated with 1% sucrose in PBS buffer (300 μl/well), incubated for one hour at room temperature, then aspirated and dried with compressed air. The plates were packed in sealed plastic bags and stored at 4° C. and 37° C. The plates were taken out for testing at intervals from 1 to 32 days. ELISA was performed as earlier described, and the data are presented in FIG. 17. All data are normalized relative to day zero. No drop in signal was detected during the storage period, but a storage temperature of 37° C. consistently gave a slightly lower signal than at 4° C..

Example 5
UV Grafting of Anthraquinone Nitrolotriacetic Acid (NTA) Derivative 20 onto Polystyrene Surfaces The anthraquinone NTA derivative 20 was dissolved in phosphate buffer (pH 5.5) to a start concentration of 1 mM. A two fold dilution series of the solution was made 30 in two Nunc-Immuno™ Module F16 PolySorp plates (100 μl/well) and incubated for 1 hour at 50° C. The wells were aspirated and one plate was placed 14 cm below the UV-lamp (Philips HPA 400) and irradiated with UV-light for 5 minutes while the other plate was kept in the dark as control. All wells were washed with demineralized water followed by the addition of crystal violet solution (15 mg in 100 ml demineralized water; 100 μl/well) and incubated at r.t. for 30 minutes. The plates were washed with water and dried at 60° C. for 1 hour. Dissolution of bound crystal violet was done by adding a solution of 1M Hcl in ethanol to each well. The results were read on an InterMed Immuno reader NJ 200 at 590 nm. The results are shown in FIG. 11 and shows a significant increase in signal with increasing concentration of the photoprobe. No signal was obtained in the wells that had not been UV-irradiated.

Metal chelates, especially nickel chelates, hare been reported to have specific binding properties for histidine tagged peptides and proteins (Hochuli et al., J. Chromat. 411, 177–184 (1987). To test the ability of the new NTA-derivatized microtitre plates to selectively bind histidine tagged peptides three biotinylated peptides, with and without a hexahistidine tag, were synthesized by standard Fmoc solid phase peptide synthesis (the three peptides were prepared similarly to the anthraquinone substituted peptide (compound 19) in example 1).

Figure 18A:
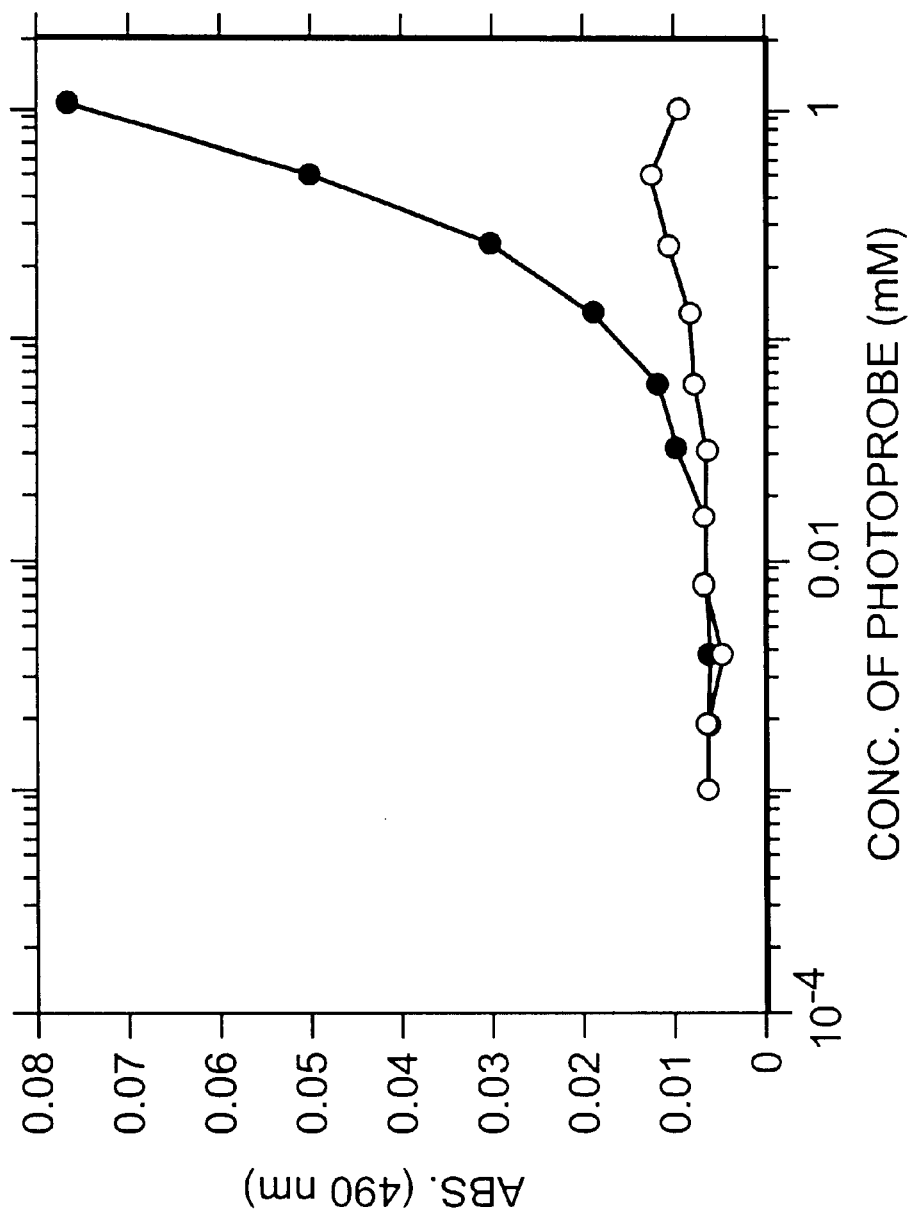
FIG. 18a shows UV grafting of anthraquinone NTA derivative 20 onto polystyrene surfaces. Effect of photoprobe concentration. Open symbols: results with no UV irradiation (control); closed symbols: results after 5 min UV irradiation.
Figure 18B:
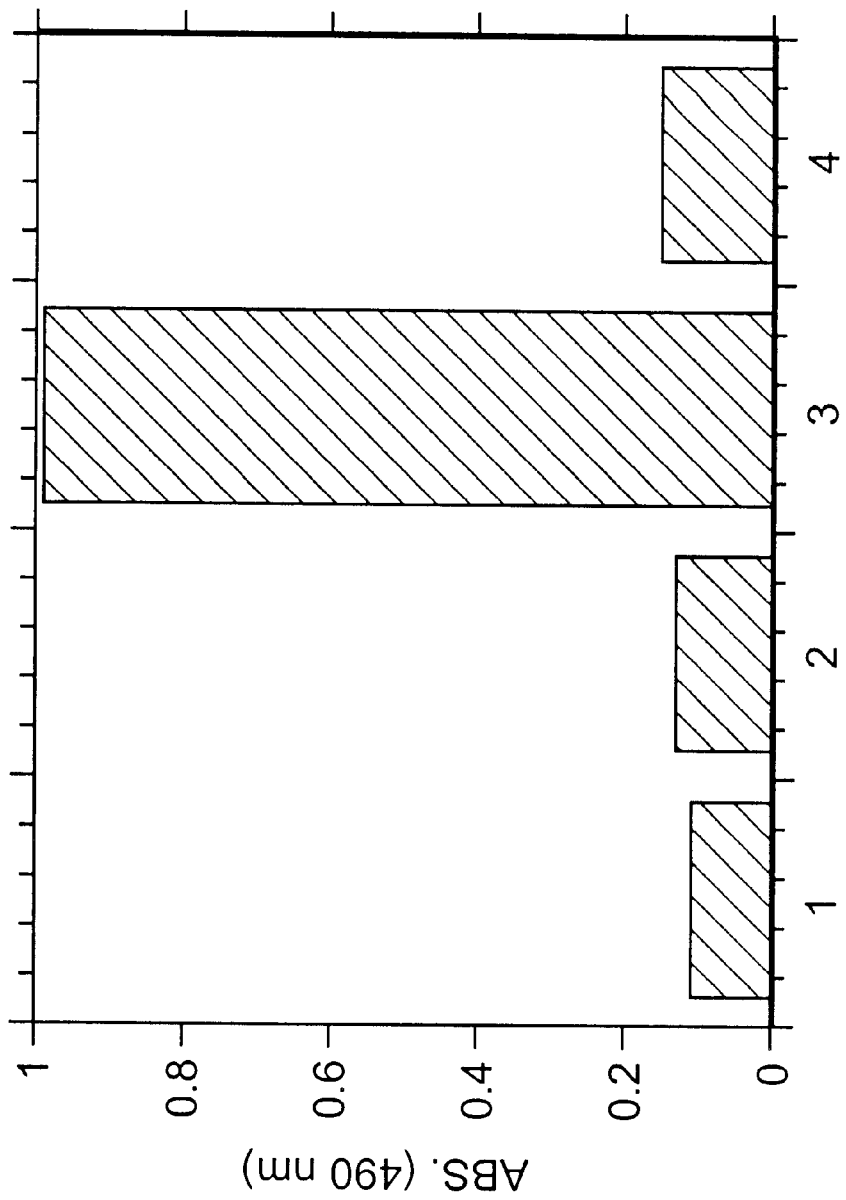
FIG. 18b shows binding of a biotinylated histidine tagged peptide onto NTA modified polystyrene surfaces. 1: no peptide added (control); 2: binding of biotinylated non-histidine tagged peptide biotin-εAhx-Leu-Lys-Leu-Lys-Trp-Lys-OH (control); 3: binding of biotinylated histidine tagged peptide biotin-εAhx-Leu-Lys-Leu-Lys-Trp-Lys-His-His-His-His-His-His-OH; 4: binding of biotinylated non-histidine tagged peptide biotin-εAhx-Arg-Thr-Gln-Asp-Glu-Asn-Pro-Val-Val-His-Phe-Lys-Asn-Ile-Val-Thr-Pro-Arg-Thr-Pro-OH (control).
Figure 19:
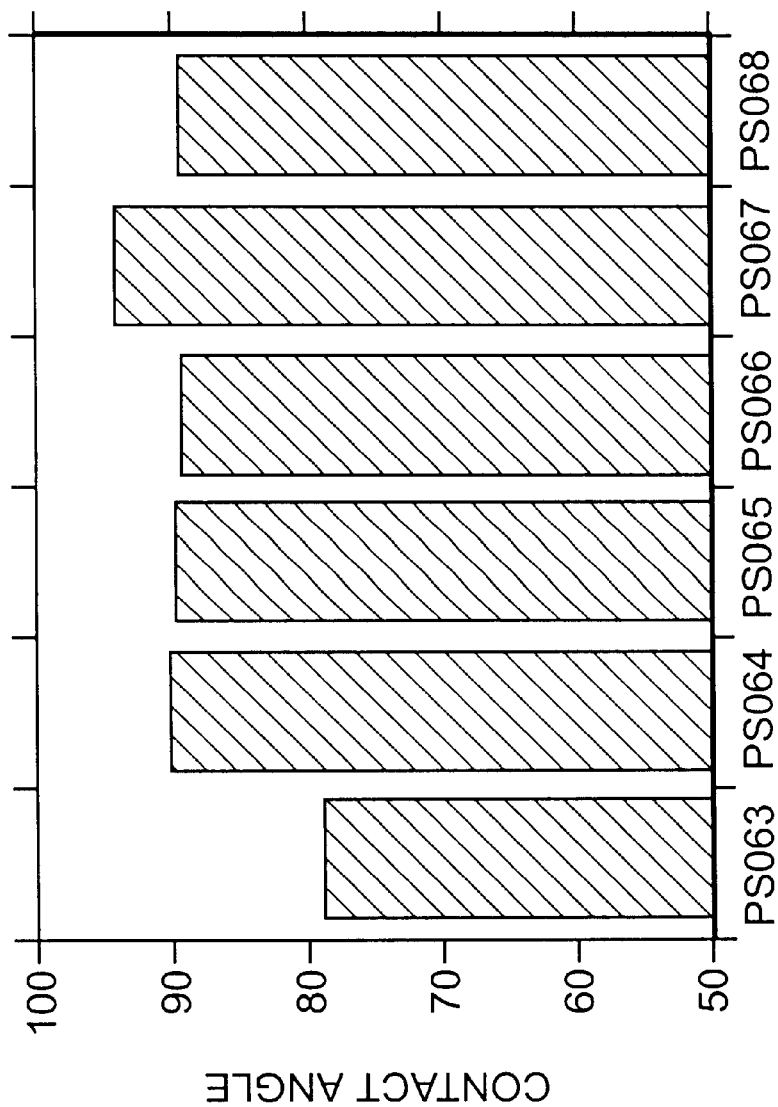
FIG. 19 shows UV grafting of the anthraquinone PEG2000 derivative 22 onto polystyrene surfaces. PS063: 0.3 mM photoprobe, 5 min UV irradiation; PS064: 0.3 mM photoprobe, no UV irradiation (control); PS065: 0.3 mM PEG2000, 5 min UV irradiation (control); PS066: 0.3 mM PEG2000, no UV irradiation (control); PS067: $H_2O$ alone, 5 min UV irradiation (control); PS068: $H_2O$ alone, no UV irradiation (control).
Figure 20:
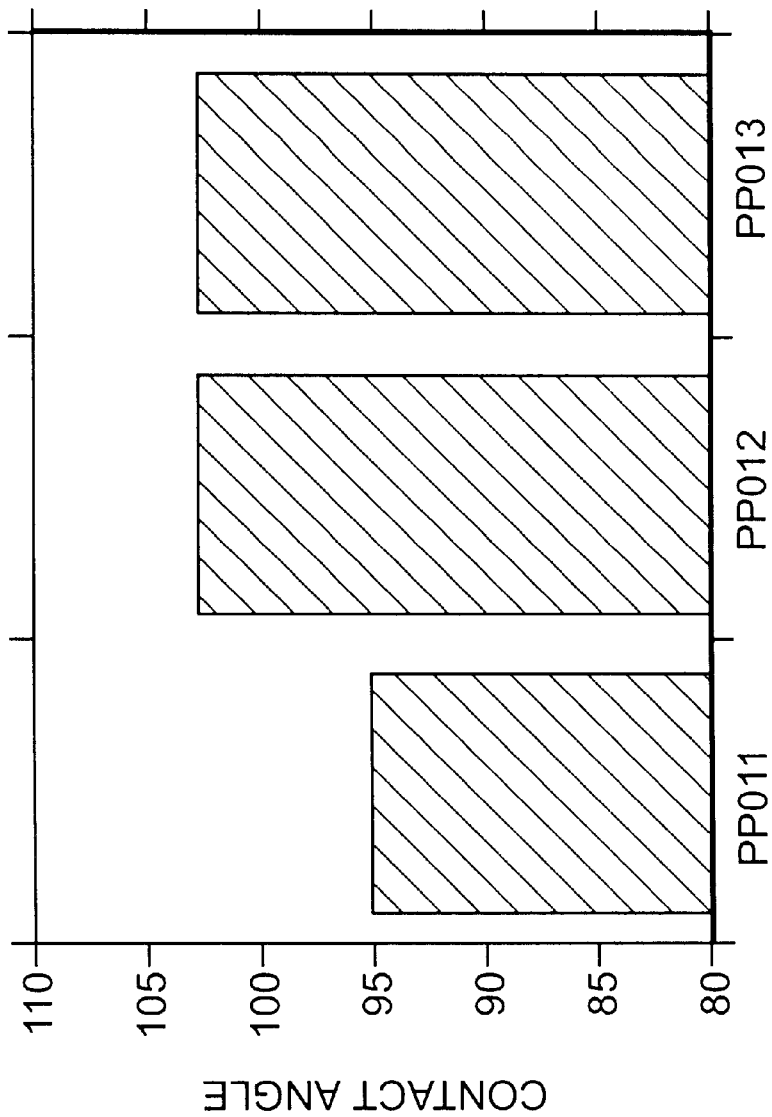
FIG. 20 shows UV grafting of the anthraquinone PEG2000 derivative 22 onto polypropylene surfaces. PP011: 0.3 mM photoprobe, 5 min UV irradiation; PP012: 0.3 mM photoprobed no UV irradiation (control); PP013: $H_2O$ alone, no UV irradiation (control).

Peptide 1: Biotin-εAhx-Leu-Lys-Leu-Lys-Trp-Lys-OH
Peptide 2: Biotin-εAhx-Leu-Lys-Leu-Lys-Trp-Lys-His-His-His-His-His-His-OH
Peptide 3: Biotin-εAhx-Arg-Thr-Gln-Asp-Glu-Asn-Pro-Val-Val-His-Phe-Phe-Lys-Asn-Ile-Val-Thr-Pro-Arg-Thr-Pro-OH Photocoupling of the anthraquinone substituted NTA derivative was done as described above except that the plate was irradiated with UV-light for 10 min without prior aspiration of the solution. The plate was washed three times with PBS buffer (pH 7.2) and then charged with nickel by adding NiSO$_4$ (50 mM in Milli Q water, 100 μl/well). After incubation for 30 min at room temperature the wells were washed three times with Milli Q water. Solutions of each peptide (23 μM, 100 μl/well) in the assay buffer (PBS buffer (pH 7.2) containing 0.05% Tween 20® and 500 mM NaCl) were added to separate rows of the plate. Water was added to the rest of the rows as control. The peptides were allowed to incubate overnight at room temperature, then the wells were washed three times with the assay buffer, and avidin mix (100 μl/well, for details see example 3) in the assay buffer added to the wells. After two hours at room temperature the wells were emptied, washed three times with assay buffer, and the amount of immobilized avidin quantified by measuring the peroxidase activity (for details see example 3). The results are shown in FIG. 18a and clearly show that only the histidine tagged peptide gave any significant binding in the nickel chelate plate.

Example 6
UV-grafting of Anthraquinone Substituted Polyethylene Glycol 2000 (AO—CO-PEG2000) Derivative 22 onto Polystyrene Surfaces The anthraquinone PEG2000 derivative 22 was dissolved in Milli Q water to a concentration of 0.3 mM. Polystyrene slides (from Nunc, Denmark) were rinsed with 96% ethanol (1×5 minutes with ultrasonication) and Milli Q water (2×5 minutes with ultrasonication) and dried in a non-evacuated desiccator above CaCl$_2$ (residual water in the atmosphere above the CaCl$_2$: 0.14–1.4 mg/l). Before photoimmobilization the slides were brought into equilibrium with the natural water content in the atmosphere. Two slides were placed in a small metal container and the photoprobe solution added to cover the surface of the slide with approx. 2.5 mm of the solution above the surface. One of the slides was placed 10 cm below the UV-lamp (Philips HPA 400) and irradiated for 5 minutes, while the other slide was kept in the dark as control. Both slides were rinsed thoroughly with Milli Q water from a bottle and then three times with Milli Q water with ultrasonication (3×5 minutes). The slides were dried in a non-evacuated desiccator above CaCl$_2$. As further controls two slides were treated as described above with a solution of PEG2000 (0.3 mM) and another two slides with Milli Q water alone. The effect of the photografting were tested by measuring the advancing contact angles using a VCA-2000 instrument (AST Products, Inc.). Five drops (1.5–2.5 μl) of Milli Q water were placed on each slide and the advancing contact angle measured (two contact angles per drop giving 10 contact angles per slide) using the manufacturers software. Prior to each series of measurements, the slides were brought into equilibrium with the natural water content in the atmosphere. The results are shown in FIG. 12 and clearly show a decrease of the advancing contact angle on the anthraquinone substituted PEG2000 photografted polystyrene slide relative to the controls.

Example 7
UV-grafting of Anthraquinone Substituted Polyethylene Glycol 2000 (AO—CO-PEG2000) Derivative 22 onto Polypropylene Surfaces The anthraquinone PEG2000 derivative 22 was dissolved in Milli Q water to a concentration of 0.3 mM. Polypropylene slides (from Nunc, Denmark) rinsed and dried as described for the polystyrene slides (Example 6). Two slides were placed in a small metal container and the photoprobe solution added to cover the surface of the slide with approx. 2.5 mm of the solution above the surface. One of the slides was placed 10 cm below the UV-lamp (Philips HPA 400) and irradiated for 5 minutes, while the other slide was kept in the dark as control. Both slides were rinsed thoroughly with Milli Q water from a bottle and then ten times with Milli Q water with ultrasonication (10×5 minutes). The slides were dried in a non-evacuated desiccator above $CaCl_2$. As a further control one slide was washed and dried as described above. Advancing contact angle measurements were performed as described for the polystyrene slides. The results are shown in FIG. 13 and clearly show a decrease in the advancing contact angle on the anthraquinone substituted PEG2000 photografted polypropylene slide relative to the controls.

We claim:

1. A method of immobilizing a ligand (L) to the surface (P) of a solid carbon-containing substrate material; said method comprising:

a photochemical step of linking the ligand (L) via a quinone (Q) to the solid carbon-containing material surface (P);

said solid carbon-containing material surface (P) being linked to the quinone (Q) either directly or via a spacer ($S_1$); and said quinone (Q) being linked to the ligand (L) either directly or via a spacer (S) and/or a thermochemically reactive compound (T);

said spacers ($S_1$) and (S) independently being thermochemically and photochemically non-reactive spacers;

wherein the quinone (Q) is selected from the group consisting of monomeric quinone compounds, dimeric quinone compounds, and oligomeric quinone compounds;

said quinone compound (Q) containing a cyclic hydrocarbon, or from 2 to 10 fused cyclic hydrocarbons, said quinone compound having at least two conjugated carbonyl groups, the number of which does not exceed twice the number of fused cyclic hydrocarbons;

said quinone compound (Q) optionally being substituted with substituents (R) which do not result in steric hindrance of the immobilization of the ligand (L) and do not disturb the photochemical step; and wherein the photochemical step comprises irradiation of the quinone (Q) with non-ionizing electromagnetic radiation having a wavelength in the range from UV to visible light.

2. A method according to claim 1, wherein the electromagnetic radiation is applied for less than 12 hours.

3. A method according to claim 1 wherein the quinone compound comprises a cyclic hydrocarbon or 2–4 fused cyclic hydrocarbons according to the general formulas

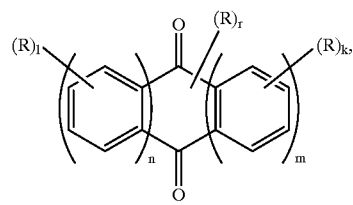
(XXXVII)

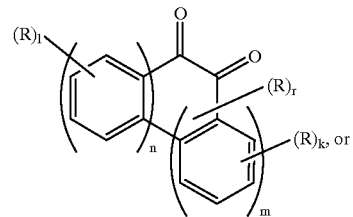
(XXXVIII)

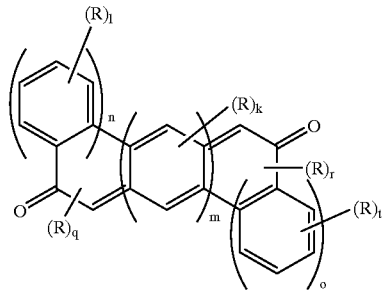
(XXXIX)

wherein the letters m, n and o designate integers from 0–8, the sum of m, n and o being at the most 8; 1 indicates an integer from 0 to two times n; r and q indicate 0, 1 or 2; k indicates 0 or an integer from 1 to 2 times m; and t indicates 0 or an integer from 1 to 2 times o.

4. A method according to claim 3, wherein the quinone compound (Q) is selected from the group consisting of anthraquinones

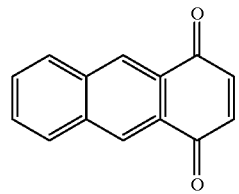
(V)

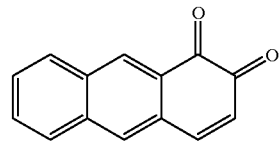
(VI)

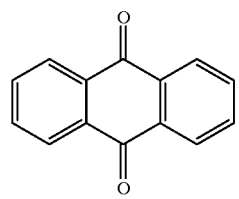
(VII)

benzoquinones
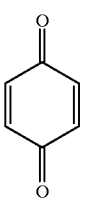
(I)
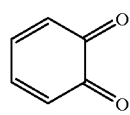
(II)
napthhoquinones
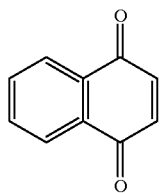
(III)
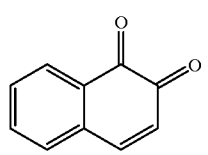
(IV)
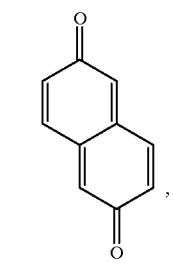
(XXVII)
and compounds
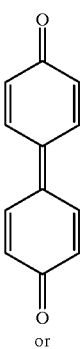
(XXVI)
or
-continued
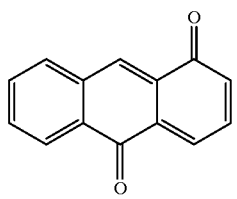
(X)
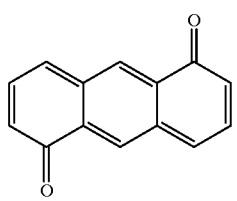
(XI)
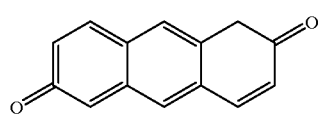
(XIII)
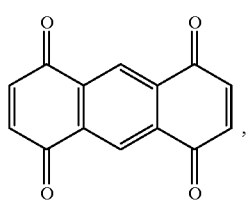
(XXVIII)
phenanthrenequinones
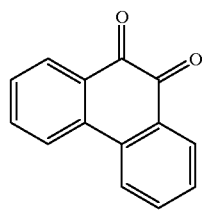
(VIII)
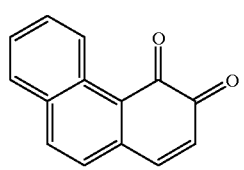
(IX)
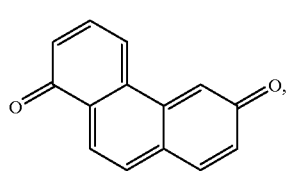
(XII)

(XXIX)

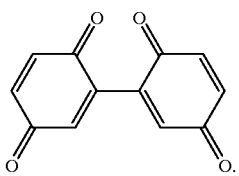

5. A method according to any of claims 1–4, wherein the quinone compound (Q) is substituted with substituents (R) selected from the group consisting of —$NO_2$, —$SO_3^-$, —$SO_2^-$; —CN, $PO_3^{2-}$, —$PO_2^-$, —COOH, halogen, (—F, —Cl, —Br, —I), primary amines, secondary amines, tertiary amines, and hydrocarbyls which may be substituted with: —$NO_2$, —$SO_3^-$, —CN, —$PO_3^{2-}$, —$PO_2^-$, —COOH, halogen, (—F, —Cl, —Br, —I), epoxide, and —H.

6. A method according to claim 1, wherein the carbon-containing material is a polymer selected from the group consisting of synthetic and natural polymers.

7. A method according to claim 1, wherein the carbon containing material (P) is selected from the group consisting of carbon-containing silica, carbon-containing glass, carbon-containing controlled pore glass, carbon-containing silica gel, carbon-containing metal; monolayer films, multilayer films; -Langmuir-Blodgett-films; biological membranes; natural polymers coated with biological or organic material; and synthetic polymers coated with biological or organic material.

8. A method according to claim 1, wherein the ligand (L) is selected from the group consisting of —COOH (carboxylic acids), sulfonic acid derivatives, —COOR (esters), —COX (acid halides, acid fluorides and acid chlorides, acid azides), —$CONHNH_2$ (acid hydrazides), —$NHCONHNH_2$ (semicarbazides), —$NHCSNHNH_2$ (thiosemicarbazides), —CN (nitriles), —CHO (aldehydes), RR'CO (ketones), —OH (alcohols), —SH (thiols), —SSR (disulfides), —$NH_2$ (primary amines), —NH— (secondary amines), >N-(tertiary amines), —$NHNH_2$ (hydrazines), —OR (ethers), epoxides, —SR (sulfides), —X (halides), —$NO_2$, —$CH_3$; non-functional groups and biologically active molecules.

9. A method according to claim 1, wherein the spacer (S) is a distance making group selected from the group consisting of $C_1$–$C_{20}$ alkyl groups; polyoxyethylene; oligo/polyamides; oligosaccharides, oligo/polyphosphates; oligo/polysulfonic amides/esters; and combined units of the aforementioned.

10. A method according to claim 1, wherein the thermochemical reactive compound (T) is a compound containing a thermochemical reactive group selected from the group consisting of: —COOH (carboxylic acids), sulfonic acid derivatives, —COOR (esters), —COX (acid halides, acid azides and similar carboxylic acid derivatives), —$CONHNH_2$ (acid hydrazides), —$NHCONHNH_2$ (semicarbazides), —$NHCSNHNH_2$ (thiosemicarbazides), —CHO (aldehydes), RR'CO (ketones), —OH (alcohols), —X (halides: chloride, bromide, iodide), —SH thiols, —SSR (disulfides), —$NH_2$ (primary amines), —NH— (secondary amines), >N-(tertiary amines), —$NHNH_2$ (hydrazines), epoxides and maleimides.

11. A method according to claim 1, comprising the steps of linking the quinone compound (Q) to the ligand (L) to obtain a quinone-ligand conjugate (Q-L), and photoimmobilizing the quinone-ligand conjugate (Q-L) onto the substrate material surface (P) to obtain the substrate material (P-Q-L).

12. A method according to claim 1, comprising the steps of linking the ligand (L) to the spacer molecule (S) by use of a photochemical or thermochemical compound, linking the spacer-ligand conjugate (S-L) to a quinone compound (Q) to obtain a quinone-ligand conjugate (Q-S-L) having an intermediate spacer molecule, and photoimmobilizing the quinone-ligand conjugate (Q-S-L) onto the substrate surface (P) to obtain the substrate material (P-Q-S-L).

13. A method according to claim 1, comprising the steps of linking the quinone compound (Q) to the spacer molecule (S), linking the spacer-quinone conjugate (Q-S) to the ligand (L) to obtain a quinone-ligand conjugate (Q-S-L) having an intermediate spacer molecule, and then photoimmobilizing the quinone-ligand conjugate onto the substrate surface (P) to obtain the substrate material (P-Q-S-L).

14. A method according to claim 1, comprising the steps of linking the quinone compound (Q) to the substrate surface (P) to obtain a quinone-substrate surface conjugate (P-Q), photoimmobilizing the ligand (L) to a quinone-substrate surface conjugate (P-Q) to obtain the substrate material (P-Q-L).

15. A method according to claim 1, comprising the steps of linking the spacer molecule ($S_1$) by use of a photochemical or a thermochemical compound to a substrate surface (P), linking the quinone compound (Q) to the spacer-substrate surface conjugate (P-$S_1$) to obtain a quinone-substrate surface conjugate (P-$S_1$-Q) having an intermediate spacer molecule, and photoimmobilizing the ligand (L) to a quinone-polymer surface conjugate.

16. A method according to claim 1, comprising the steps of linking the quinone compound (Q) to the spacer molecule (S), linking the spacer-quinone conjugate (Q-S) to the substrate surface to obtain a quinone-substrate surface conjugate (P-Q-S) having an intermediate spacer molecule.

17. A method according to claim 1, wherein the photochemical step takes place in an aqueous medium.

18. A carbon-containing material having a ligand (L) immobilized to its surface (P), said material being prepared according to the method as claimed in claim 1.

19. A detection system including a carbon-containing substrate material as prepared according to the method as claimed in claim 1.

20. A solid phase immunoassay including a carrier comprising a carbon-containing substrate material as prepared in claim 1.

21. The assay as claimed in claim 20, wherein the carrier is selected from the group consisting of well plates, test particles such as beads and micro spheres, test tubes, test sticks, and test strips.

22. In a method for solid phase synthesis the improvement comprising using a carrier comprising a carbon-containing substrate material as prepared in claim 1.

23. A method for immobilizing a ligand to a solid carbon-containing substrate material surface (P), the method comprising a photochemical step of linking the ligand (L) via a quinone (Q) to the solid carbon-containing material surface, wherein the quinone is utilized as a photochemically reactive coupling compound.

24. A method according to claim 23, wherein the quinone is optionally substituted with substituents (R) which do not result in steric hindrance to the immobilization of the ligand (L) and do not disturb the photochemical step.

25. A method according to claim 23 or 24, wherein the quinone compound comprises a cyclic hydrocarbon or 2–4 fused cyclic hydrocarbons according to the general formulas (XXXVII)
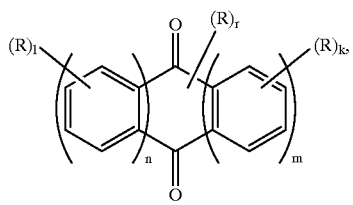

(XXXVIII)
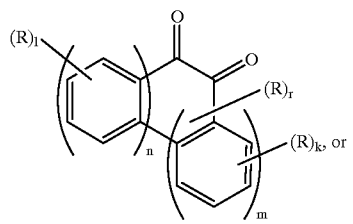

(XXXIX)
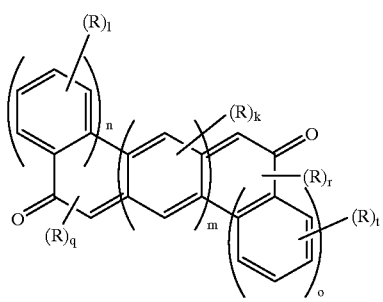

wherein the letters m, n and o designate 0–8, the sum of m, n and o is at the most 8; l indicates 0 or an integer from 1 to two times n; r and q indicate 0, 1 or 2; k indicates 0 or an integer from 1 to 2 times m; and t indicates 0 or an integer from 1 to 2 times o.

26. A method according to claim 25, wherein the quinone compound (Q) is selected from the group consisting of anthraquinones (V)
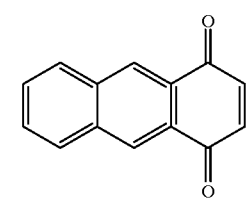

(VI)
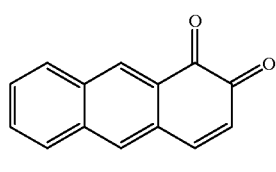

(VII)
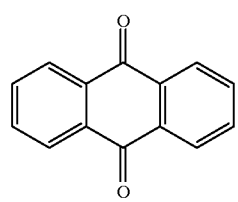

(X)
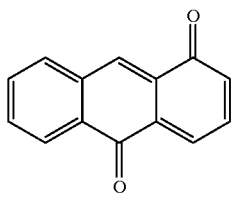

(XI)
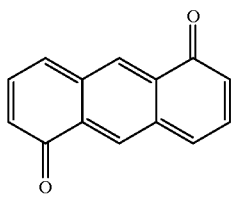

(XIII)
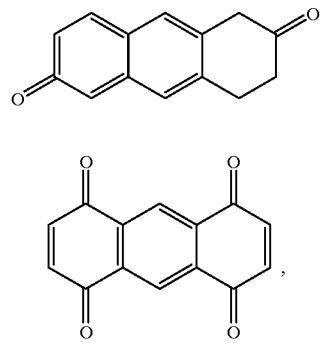

(XXVIII)
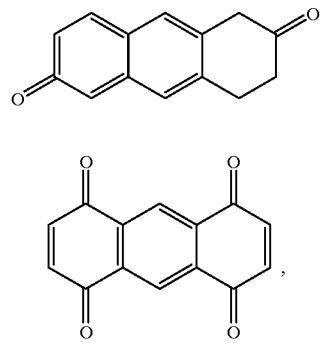

phenanthrenequinones (VIII)
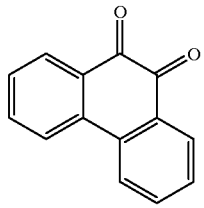

(IX)
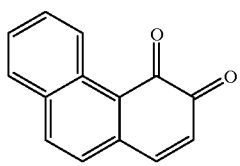

(XII)
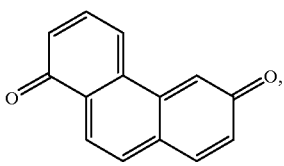

benzoquinones (I)
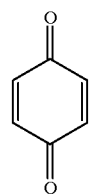

(II)
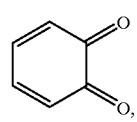, naphthoquinones (III)
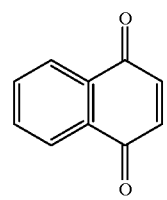

(IV)
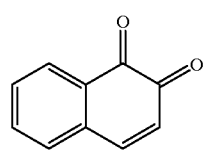

(XXVII)
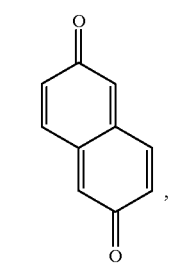, and compounds (XXVI)
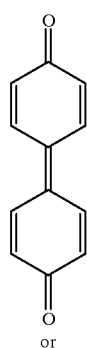

or (XXIX)
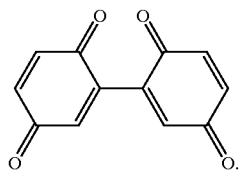.

27. A method according to claim 25, wherein the quinone compound (Q) is selected from the group consisting of anthraquinones, phenanthrenequinones, and compound (XXVI)
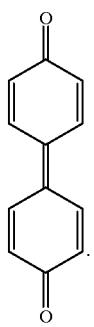.

28. A method according to claim 27, wherein the quinone compound (Q) is an anthraquinone.

29. A method according to claim 27, wherein the quinone compound (Q) is a quinone of the formula (XXVI)
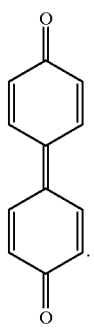.

30. A method according to claim 3, wherein the quinone compound (Q) is selected from the group consisting of anthraquinones, phenanthrenequinones, and compound

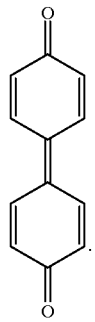

(XXVI)

31. A method according to claim 30, wherein the quinone compound (Q) is an anthraquinone.

32. A method according to claim 30, wherein the quinone compound (Q) is a compound of the formula

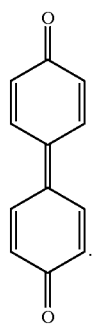

(XXVI)

33. A method according to claim 6, wherein the polymer is selected from polystyrene, polyethylene, polyvinylacetate, polyvinylchloride, polyvinylpyrrolidone, polyacrylonitrile, polymethylmethacrylate, polytetrafluoroethylene, polycarbonate, poly-4-methyl-pentylene, polyester, polypropylene, cellulose, nitrocellulose, starch, polysaccharides, natural rubber, butyl rubber, styrene butadiene rubber, and silicone rubber.

34. A method according to claim 8, wherein the ligand is a biologically active molecule selected from the group consisting of biotin, toxins, herbicides, pesticides, carbohydrates, antibiotics, cell poisons, steroids, peptides, nucleotides, peptide nucleic acids (PNA) binding partners, nucleic acid binding partners, proteins and haptenes.

* * * * *

UNITED STATES PATENT AND TRADEMARK OFFICE
CERTIFICATE OF CORRECTION

PATENT : 6,033,784
DATED : March 7, 2000
INVENTOR(S) : Mogens Havsteen JACOBSEN et al.

It is certified that error appears in the above-identified patent and that said Letters Patent is hereby corrected as shown below:

Title page, column 1, above item 51, insert the following:

--[30] Foreign Application Priority Data
April 7, 1995 [DK] Denmark......0425/95--.

Signed and Sealed this

Fifteenth Day of May, 2001

*Attest:*

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 6,033,784
DATED : March 7, 2000
INVENTOR(S) : Mogens Havsteen Jakobsen and Troels Koch It is certified that error appears in the above-identified patent and that said Letters Patent is hereby corrected as shown below:

<u>Title page,</u>
Item [76], delete "Jacobsen" and insert -- Jakobsen. --

Signed and Sealed this

Seventeenth Day of September, 2002

Attest:

JAMES E. ROGAN
Attesting Officer *Director of the United States Patent and Trademark Office*